United States Patent
Dutton et al.

(10) Patent No.: US 10,596,248 B2
(45) Date of Patent: Mar. 24, 2020

(54) IMMUNOMODULATING COMPOSITION FOR TREATMENT

(71) Applicant: Jingang Medicine (Australia) Pty Ltd, Hong Kong (HK)

(72) Inventors: Julie Dutton, Toowoomba (AU); Ian Frazer, St. Lucia (AU)

(73) Assignee: Jingang Medicine (Australia) Pty Ltd, Hong Kong (HK)

( * ) Notice: Subject to any disclaimer, the term of this patent is extended or adjusted under 35 U.S.C. 154(b) by 0 days.

(21) Appl. No.: 16/060,410

(22) PCT Filed: Dec. 9, 2016

(86) PCT No.: PCT/AU2016/051214
§ 371 (c)(1),
(2) Date: Jun. 7, 2018

(87) PCT Pub. No.: WO2017/096432
PCT Pub. Date: Jun. 15, 2017

(65) Prior Publication Data
US 2019/0134181 A1     May 9, 2019

(30) Foreign Application Priority Data

Dec. 9, 2015 (AU) .................. 2015905099

(51) Int. Cl.
| | | |
|---|---|---|
| *A61K 39/12* | (2006.01) | |
| *C07K 14/025* | (2006.01) | |
| *C07K 14/005* | (2006.01) | |
| *A61P 31/20* | (2006.01) | |
| *C12N 15/85* | (2006.01) | |
| *A61K 39/00* | (2006.01) | |

(52) U.S. Cl.
CPC ............. *A61K 39/12* (2013.01); *A61P 31/20* (2018.01); *C07K 14/005* (2013.01); *C07K 14/025* (2013.01); *C12N 15/85* (2013.01); *A61K 2039/53* (2013.01); *C07K 2319/95* (2013.01); *C12N 2710/20022* (2013.01); *C12N 2710/20032* (2013.01); *C12N 2710/20034* (2013.01)

(58) Field of Classification Search
None
See application file for complete search history.

(56) References Cited

U.S. PATENT DOCUMENTS

2011/0020374 A1* 1/2011 Frazer .................. A61K 39/145
                                                424/184.1
2012/0053509 A1* 3/2012 Weiner .................. A61K 39/12
                                                604/20

FOREIGN PATENT DOCUMENTS

| WO | WO-92/16636 | 10/1992 |
| WO | WO-1996/019496 | 6/1996 |
| WO | WO-01/19408 | 3/2001 |
| WO | WO-2009/049350 | 4/2009 |

OTHER PUBLICATIONS

Bravo et al., "Codon usage in papillomavirus genes: practical and functional aspects," Papillomavirus Report (2005) 16(2):63-72.
Dutton et al., "A novel DNA vaccine technology conveying protection against a lethal herpes simplex viral challenge in mice," PLOS One (2013) 8(10):e76407.
Liu et al., "Codon Modified Human Papillomavirus Type 16 E7 DNA Vaccine Enhances Cytotoxic T-Lymphocyte Induction and Anti-tumour Activity," Virology (2002) 301:43-52.
Liu et al., "Polynucleotide viral vaccines: codon optimisation and ubiquitin conjugation enhances prophylactic and therapeutic efficacy," Vaccine (2002) 20:862-869.
Zhao et al., Codon usage roles in human papillomavirus, Rev Med Virol (2011) 21:397-411.
Cid-Arregui et al., "A synthetic E7 gene of human papillomavirus type 16 that yields enhanced expression of the protein in mammalian cells and is useful for DNA immunization studies", Journal of Virology (2003) 77(8):4928-4937.
Liu et al., "Polynucleotide viral vaccines: codon optimization and ubiquitin conjugation enhances prophylactic and therapeutic efficacy", Vaccine (2002) 862-869.
Yan et al., "Induction of antitumor immunity in vivo following delivery of a novel HPV-16 DNA vaccine encoding an E6/E7 fusion antigen", Vaccine (2009) 27:431-440.
Zhao et al., "Codon usage bias and A+T content variation in human papillomavirus genomes", Virus Research (2003) 98:95-104.
Zhou et al., "Papillomavirus capsid protein expression level depends on the match between codon usage and tRNA availability", Journal of Virology (1999) 73(6):4972-4982.

* cited by examiner

*Primary Examiner* — Nianxiang Zou
(74) *Attorney, Agent, or Firm* — Morrison & Foerster LLP

(57) ABSTRACT

Disclosed are therapeutic compositions and methods for inducing an immune response to human papillomavirus (HPV). More particularly, disclosed is a method for inducing an immune response in a subject by introducing and expressing a nucleic acid molecule encoding an immunogenic HPV antigen.

19 Claims, 6 Drawing Sheets

Specification includes a Sequence Listing.

B

IMMUNOMODULATING COMPOSITION FOR TREATMENT

RELATED APPLICATIONS

This application is a U.S. National Stage of International Application No. PCT/AU2016/051214 filed on Dec. 9, 2016, which claims priority to Australian Provisional Application No. 2015905099 entitled "Immunomodulating Compositions for Treatment", filed on 9 Dec. 9, 2015, the entire contents of which are hereby incorporated herein by reference in their entirety.

INCORPORATION BY REFERENCE OF SEQUENCE LISTING

The present application is being filed along with a Sequence Listing in electronic format. The Sequence Listing is provided as a file entitled 35285357_ST25.TXT, created Nov. 23, 2018, which is 19,021 bytes in size. The information in the electronic format of the Sequence Listing is incorporated by reference in its entirety.

FIELD OF THE INVENTION

This invention relates generally to the field of therapeutic compositions and methods for inducing an immune response to human papillomavirus (HPV). More particularly, the invention relates to a method for inducing an immune response in a subject by introducing and expressing a nucleic acid molecule encoding an immunogenic HPV antigen.

BACKGROUND OF THE INVENTION

Papillomaviruses are small DNA viruses that infect a number of animal species. Over 60 different types of human papillomavirus (HPV) have been identified, which infect a variety of body locations and are responsible for common skin warts, laryngeal papillomas, genital warts and other wart-like lesions. Genital HPV infections are particularly common; a number of HPV types, but most frequently types 6, 11, 16 and 18, infect the genital tract in both men and women. In women, HPVs infect various portions of the genital tract including the cervix.

Genital HPVs are clearly a significant clinical problem. A 2010 study (HPV Infection and Transmission in Couples through Heterosexual activity) found that more than half (56%) of young adults in new sexual relationships were infected with HPV. Of those, nearly half (44%) were infected with an HPV type that causes cancer. Further, the World Health Organization estimates that around 530,000 women are diagnosed with cervical cancer and 275,128 die from the disease annually, rating the disease as the second most common cancer among 15 to 44 year-old women.

SUMMARY OF THE INVENTION

The present invention is predicated in part on the inventors' realization that a binary nucleic acid construct system with enhanced production of qualitatively different forms of a synthetic HPV E6-E7 fusion protein would elicit a significant immune response. Based on this consideration, it is proposed that it would be particularly suited to therapeutic applications for combating human papillomavirus (HPV) infections, as described hereafter.

Accordingly, in one aspect the present invention provides a construct system for the treatment of an HPV infection, wherein the construct system comprises, consists, or consists essentially of a first nucleic acid construct and a second nucleic acid construct, wherein the first construct comprises, consists, or consists essentially of a first synthetic coding sequence that encodes a first polypeptide sequence comprising an HPV E6 amino acid sequence conjugated to a HPV E7 amino acid sequence, wherein the HPV E6 and E7 amino acid sequences are both distinguished from a wild-type HPV E6 and E7 coding sequences, respectively, by the replacement of selected codons in the wild-type HPV E6 or E7 coding sequence with synonymous codons, wherein an individual synonymous codon has a preference for producing a greater immune response than a corresponding selected codon, wherein the codon replacements are selected from TABLE 1, wherein at least about 70%, 75%, 80%, 85%, 90%, 91%, 92%, 93%, 94%, 95%, 96%, 97%, 98%, 99%, or 100%, of the codons for the first synthetic coding sequence are synonymous codons according to TABLE 1, and wherein the first synthetic coding sequence is operably connected to a regulatory nucleic acid sequence; and wherein the second construct comprises, consists, or consists essentially of a second synthetic coding sequence that encodes a first polypeptide sequence comprising an HPV E6 amino acid sequence conjugated to a HPV E7 amino acid sequence, wherein the HPV E6 and E7 amino acid sequences are both distinguished from wild-type HPV E6 and E7 coding sequences, respectively, by the replacement of selected codons in the wild-type HPV E6 or E7 coding sequence with synonymous codons, wherein an individual synonymous codon has a preference for producing a greater immune response than a corresponding selected codon, wherein the codon replacements are selected from TABLE 1, and wherein at least about 70%, 75%, 80%, 85%, 90%, 91%, 92%, 93%, 94%, 95%, 96%, 97%, 98%, 99%, or 100%, of the codons for the first synthetic coding sequence are synonymous codons according to TABLE 1, and wherein the first synthetic coding sequence is operably connected to a regulatory nucleic acid sequence; and to a nucleic acid sequence that encodes a ubiquitin molecule; and wherein TABLE 1 is as follows:

TABLE 1

| First Codon | Synonymous Codon |
|---|---|
| $Ala^{GCG}$ | $Ala^{GCT}$ |
| $Ala^{GCG}$ | $Ala^{GCC}$ |
| $Ala^{GCA}$ | $Ala^{GCT}$ |
| $Ala^{GCA}$ | $Ala^{GCC}$ |
| $Ala^{GCC}$ | $Ala^{GCT}$ |
| $Arg^{CGG}$ | $Arg^{CGA}$ |
| $Arg^{CGG}$ | $Arg^{CGC}$ |
| $Arg^{CGG}$ | $Arg^{CGT}$ |
| $Arg^{CGG}$ | $Arg^{AGA}$ |
| $Arg^{AGG}$ | $Arg^{CGA}$ |
| $Arg^{AGG}$ | $Arg^{CGC}$ |
| $Arg^{AGG}$ | $Arg^{CGT}$ |
| $Arg^{AGG}$ | $Arg^{AGA}$ |
| $Asn^{AAT}$ | $Asn^{AAC}$ |
| $Asp^{GAT}$ | $Asp^{GAC}$ |
| $Cys^{TGT}$ | $Cys^{TGC}$ |
| $Glu^{GAG}$ | $Glu^{GAA}$ |
| $Gly^{GGC}$ | $Gly^{GGA}$ |
| $Gly^{GGT}$ | $Gly^{GGA}$ |
| $Gly^{GGG}$ | $Gly^{GGA}$ |
| $Ile^{ATA}$ | $Ile^{ATC}$ |
| $Ile^{ATA}$ | $Ile^{ATT}$ |

TABLE 1-continued

| First Codon | Synonymous Codon |
|---|---|
| Ile$^{ATT}$ | Ile$^{ATC}$ |
| Leu$^{TTA}$ | Leu$^{CTG}$ |
| Leu$^{TTA}$ | Leu$^{CTC}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTG}$ |
| Leu$^{TTG}$ | Leu$^{CTC}$ |
| Leu$^{TTG}$ | Leu$^{CTA}$ |
| Leu$^{TTG}$ | Leu$^{CTT}$ |
| Leu$^{CTT}$ | Leu$^{CTG}$ |
| Leu$^{CTT}$ | Leu$^{CTC}$ |
| Leu$^{CTA}$ | Leu$^{CTG}$ |
| Leu$^{CTA}$ | Leu$^{CTC}$ |
| Phe$^{TTC}$ | Phe$^{TTT}$ |
| Pro$^{CCG}$ | Pro$^{CCC}$ |
| Pro$^{CCG}$ | Pro$^{CCT}$ |
| Pro$^{CCA}$ | Pro$^{CCC}$ |
| Pro$^{CCA}$ | Pro$^{CCT}$ |
| Pro$^{CCT}$ | Pro$^{CCC}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGT}$ | Ser$^{TCC}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACC}$ |
| Thr$^{ACT}$ | Thr$^{ACA}$ |
| Thr$^{ACA}$ | Thr$^{ACG}$ |
| Thr$^{ACA}$ | Thr$^{ACC}$ |
| Thr$^{ACC}$ | Thr$^{ACG}$ |
| Tyr$^{TAT}$ | Tyr$^{TAC}$ |
| Val$^{GTA}$ | Val$^{GTG}$ |
| Val$^{GTA}$ | Val$^{GTC}$ |
| Val$^{GTA}$ | Val$^{GTT}$ |
| Val$^{GTT}$ | Val$^{GTG}$ |
| Val$^{GTT}$ | Val$^{GTC}$ |

As described above, the second nucleic acid construct of the invention encodes a ubiquitin molecule. The role of the ubiquitin molecule is to increase the rate of intracellular proteolytic degradation, relative to the polypeptide encoded by the first construct. Suitably, the ubiquitin molecule is of mammalian origin, more preferably of human or other primate origin. In a preferred embodiment of this type, the ubiquitin nucleic acid sequence comprises at least a portion of the sequence set forth in SEQ ID NO: 5, which encodes three repeats of the amino acid sequence set forth in SEQ ID NO: 6 or at least a biologically active fragment thereof. In an alternative embodiment, the ubiquitin comprises two or more copies of the sequence set forth in SEQ ID NO: 6.

In some embodiments of the invention, the first synthetic coding sequence comprises the polynucleotide sequence set forth in SEQ ID NO: 7. In some of the same and other embodiments, the second synthetic coding sequence comprises the polynucleotide sequence set forth in SEQ ID NO: 8. Preferably, the first synthetic coding sequence comprises the polynucleotide sequence set forth in SEQ ID NO: 7 and the second synthetic coding sequence comprises the polynucleotide sequence set forth in SEQ ID NO: 8.

In some embodiments, the first construct and the second construct are contained in one or more expression vectors or delivered as one polynucleotide. An advantage of some expression vectors that are contemplated for use with the present invention is that they are free of a signal or targeting sequence, as described in more detail below. In some embodiments, the expression vector is also free of any antibiotic-resistance markers. In some preferred embodiments the expression vector is NTC8485, NTC8685 or NTC9385R.

In some embodiments the subject is a mammal. In the most preferred embodiments the mammal is a human.

In another aspect, the present invention provides a method of treating HPV infection in a subject, the method comprising administering concurrently to the subject an effective amount of a construct system as described above and elsewhere herein.

In some embodiments, the method comprises identifying that the subject has an HPV infection prior to administering concurrently the first and second constructs. An advantage of this step is that the subject can be treated for HPV infection once the presence of HPV is established in the subject. Accordingly, any unnecessary expense of administering the constructs to a subject that does not have an HPV infection is avoided.

In yet another aspect of the invention the construct system as described above and elsewhere herein, is manufactured in a pharmaceutical composition which is formulated with a pharmaceutically acceptable carrier, diluent, and/or excipient. In some embodiments of this type, the pharmaceutical composition is administered with an adjuvant. In other embodiments the pharmaceutical composition is administered without an adjuvant. In other embodiments the pharmaceutical composition is administered with a reagent to promote its uptake into cells.

Accordingly, in some embodiments the present invention encompasses the use of the construct system as described above and elsewhere herein in the manufacture of a medicament for the treatment of a HPV infection.

BRIEF DESCRIPTION OF THE DRAWINGS

An example of the present invention will now be described with reference to the accompanying drawings, in which:—

TABLE 2

BRIEF DESCRIPTION OF THE SEQUENCES

Figure 1:
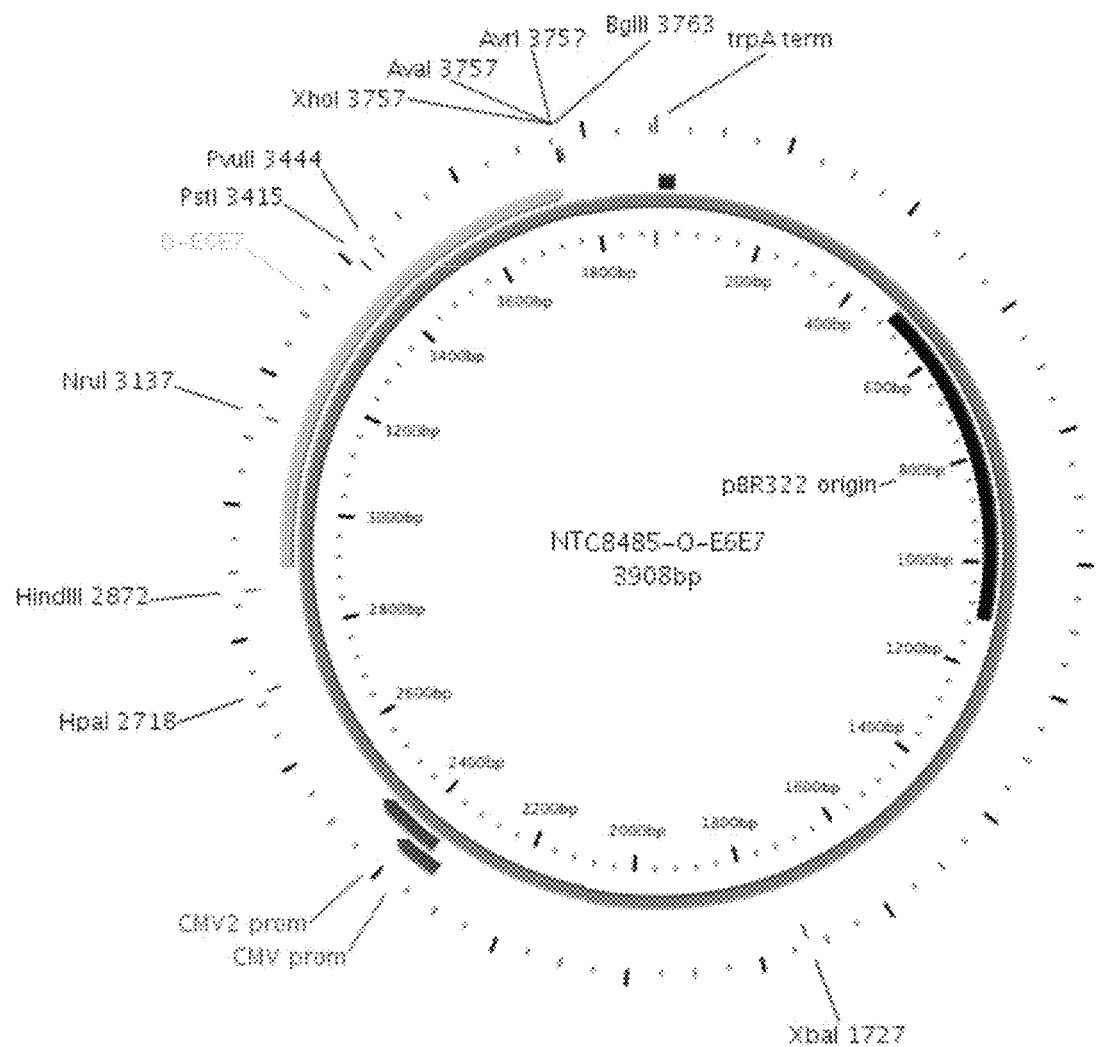
FIG. 1 shows schematic maps of NTC8485-O-sE6[C70G, I135T]-AGA-E7[C24G, E26G] and NTC8485-O-Ubi-E6 [C70G, I135T]-AGA-E7[C24G, E26G]. NTC8485 vector map showing the location of the first synthetic coding sequence (A) O-sE6[C70G, I135T]-AGA-E7[C24G, E26G] (abbreviated as O-E6E7), and (B) O-Ubi-E6[C70G, I135T]-AGA-E7[C24G, E26G] (abbreviated as O-Ubi-E6E7). Pink bars: open reading frame; black bars: origin of replication; green bars: promoters; brown bars: terminator; blue bars: unique restriction sites.
Figure 1:
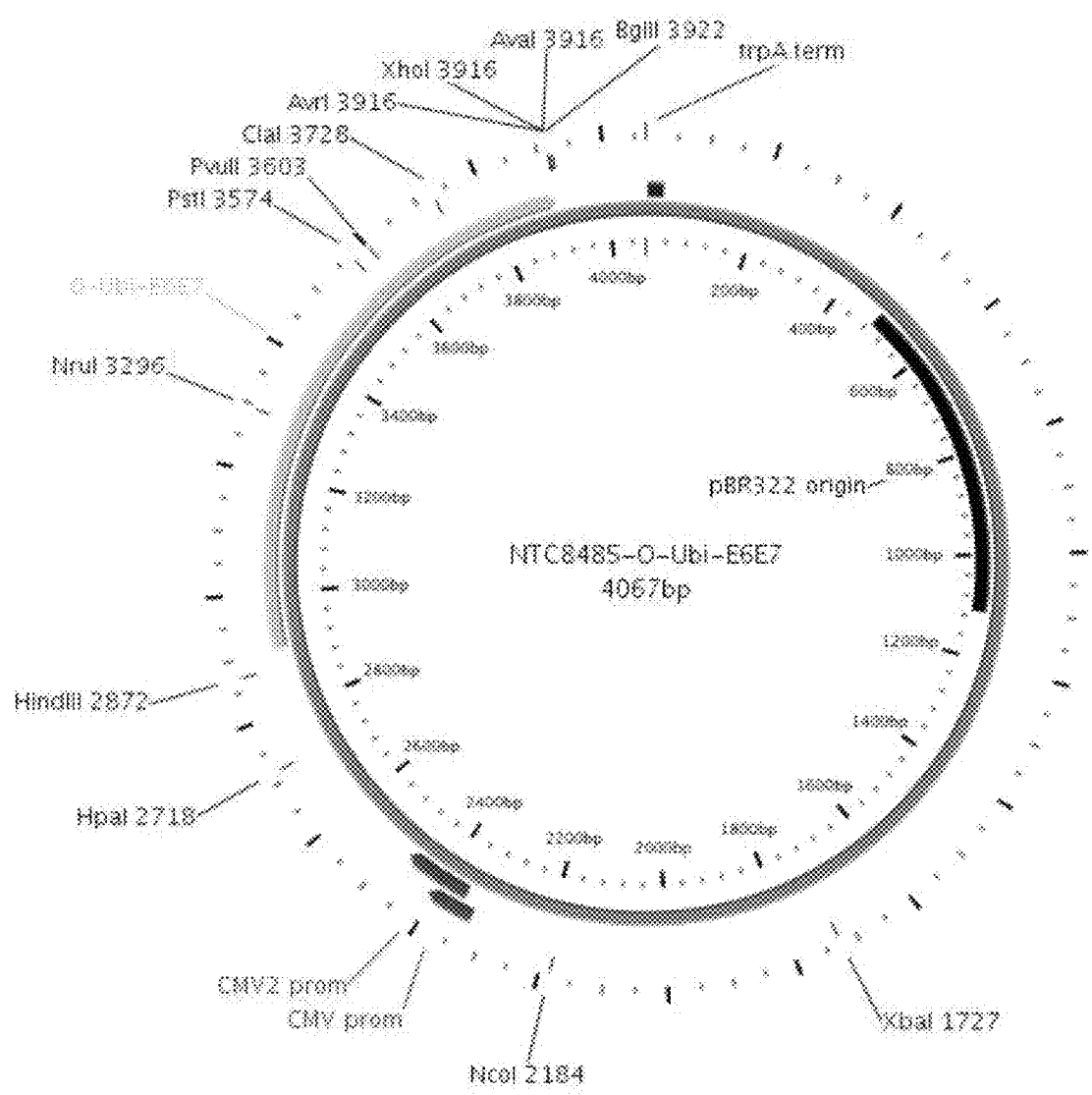

| SEQUENCE ID NUMBER | SEQUENCE | LENGTH |
|---|---|---|
| SEQ ID NO: 1 | Wild-type HPV16 E6 nucleic acid sequence (GenBank Accession No. NC_001526.2) | 477 nts |
| SEQ ID NO: 2 | Wild-type HPV16 E6 amino acid sequence (UniProt Accession No. NP_041325.1) | 158 aa |
| SEQ ID NO: 3 | Wild-type HPV16 E7 nucleic acid sequence (GenBank Accession No. KM058618) | 297 nts |
| SEQ ID NO: 4 | Wild-type HPV16 E7 amino acid sequence (UniProt Accession No. P03129) | 98 aa |
| SEQ ID NO: 5 | Human ubiquitin B coding sequence (GenBank Accession No. NM_018955) | 690 nts |
| SEQ ID NO: 6 | Human ubiquitin polypeptide (CD Accession No. cd01803) | 76 aa |
| SEQ ID NO: 7 | sE6[C70G, I135T]-AGA-E7[C24G, E26G] | 849 nts |
| SEQ ID NO: 8 | Ubi-E6[C70G, I135T]-AGA-E7[C24G, E26G, | 1008 nts |
| SEQ ID NO: 9 | E26G] NTC8485-O-s-E6[C70G, I135T]-AGA-E7[C24G, E26G] | 3908 nts |
| SEQ ID NO: 10 | NTC8485-O-Ubi-E6[C70G, I135T]-AGA-E7[C24G, E26G] | 4067 nts |

DETAILED DESCRIPTION OF THE INVENTION

I. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, frequency, percentage, dimension, size, or amount that varies by no more than 15%, and preferably by no more than 10%, 9%, 8%, 7%, 6%, 5%, 4%, 3%, 2%, 1% to a reference quantity, level, value, frequency, percentage, dimension, size, or amount.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and preferably within less than about one to about four hours. When administered contemporaneously, the agents are suitably administered at the same site on the subject, or at different sites on the subject (for example, administration to both left arm and right arm). The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

As used herein, "and/or" refers to and encompasses any and all possible combinations of one or more of the associated listed items, as well as the lack of combinations when interpreted in the alternative (or).

The terms "antigen" and "epitope" are well understood in the art and refer to the portion of a macromolecule which is specifically recognized by a component of the immune system, e.g., an antibody or a T-cell antigen receptor. Epitopes are recognized by antibodies in solution, e.g., free from other molecules. Epitopes are recognized by T-cell antigen receptor when the epitope is associated with a class I or class II major histocompatability complex molecule. A "CTL epitope" is an epitope recognized by a cytotoxic T lymphocyte (usually a $CD8^+$ cell) when the epitope is presented on a cell surface in association with an MHC Class I molecule.

It will be understood that the term "between" when used in reference to a range of numerical values encompasses the numerical values at each endpoint of the range. For example, a composition comprising between 30 μg and about 1000 μg of synthetic construct is inclusive of a composition comprising 30 μg of synthetic construct and a composition comprising 1000 μg of synthetic construct.

As used herein, the term "cis-acting sequence" or "cis-regulatory region" or similar term shall be taken to mean any sequence of nucleotides which is derived from an expressible genetic sequence wherein the expression of the genetic sequence is regulated, at least in part, by the sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector or RNA, or can be contained within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3$^{rd}$ edition Volumes 1, 2, and 3; J. F. Sambrook, D. W. Russell, and N. Irwin, Cold Spring Harbor Laboratory Press, 2000.

The term "delayed type hypersensitivity" (also termed type IV hypersensitivity) as used herein refers to a cell-mediated immune response comprising $CD4^+$ and/or $CD8^+$ T cells. $CD4^+$ helper T cells recognize antigens presented by Class II MHC molecules on antigen-presenting cells (APC). The APC in this case are often IL-12-secreting macrophages, which stimulate the proliferation of further $CD4^+$ Th1 cells. These $CD4^+$ T cells, in turn, secrete IL-2 and IFN-γ, further inducing the release of other Th1 cytokines, and thus mediating a substantial cellular immune response. The $CD8^+$ T cells function to destroy target cells on contact, whereas activated macrophages produce hydrolytic enzymes on exposure to intracellular pathogens. DTH responses in the skin are commonly used to assess cellular immunity in vivo (see, Pichler et al, 2011). Specifically, after dermal or subdermal administration, suitably intradermal administration, of an antigen, occurrence of induration and erythema at about 48 hours post-injection are strongly indicative of a positive DTH reaction, and a substantial cellular immune response.

By "effective amount," in the context of modulating an immune response or treating a disease or condition, is meant the administration of that amount of composition to an individual in need thereof, either in a single dose or as part of a series, that is effective for achieving that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

It will be understood that "eliciting" or "inducing" an immune response as contemplated herein includes stimulating a new immune response and/or enhancing a previously existing immune response.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The terms "enhancing an immune response," "producing a stronger immune response" and the like refer to increasing an animal's capacity to respond to an HPV E6 or HPV E7 polypeptide, which can be determined for example by detecting an increase in the number, activity, and ability of the animal's cells that are primed to attack such an antigen and/or an increase in the titer or activity of antibodies in the animal, which are immuno-interactive with the HPV E6 or HPV E7 polypeptide. Strength of immune response can be measured by standard immunoassays including: direct measurement of antibody titers or peripheral blood lymphocytes; cytolytic T lymphocyte assays; assays of natural killer cell cytotoxicity; cell proliferation assays including lymphoproliferation (lymphocyte activation) assays; immunoassays of immune cell subsets; assays of T-lymphocytes specific for the antigen in a sensitized subject; skin tests for cell-mediated immunity; etc. Such assays are well known in the art. See, e.g., Erickson et al., 1993, *J. Immunol.* 151:4189-4199; Doe et al., 1994, *Eur. J. Immunol.* 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., 1998, *J. Exp. Med.* 187(9) 1367-1371; Mcheyzer-Williams, M. G., et al., 1996, *Immunol. Rev.* 150:5-21; Lalvani, A., et al., 1997, *J. Exp. Med.* 186:859-865). Any statistically significant increase in strength of immune response as measured for example by immunoassay is considered an "enhanced immune response" or "immunoenhancement" as used herein. Enhanced immune response is also indicated by physical manifestations such as inflammation, as well as healing of systemic and local infections, and reduction of symptoms in disease, e.g., lesions and warts. Such physical manifestations also encompass "enhanced immune response" or "immunoenhancement" as used herein.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence.

By "expression vector" is meant any autonomous genetic element capable of directing the synthesis of a protein encoded by the vector. Such expression vectors are known by practitioners in the art.

The term "gene" as used herein refers to any and all discrete coding regions of a genome, as well as associated non-coding and regulatory regions. The gene is also intended to mean an open reading frame encoding one or more specific polypeptides, and optionally comprising one or more introns, and adjacent 5' and 3' non-coding nucleotide sequences involved in the regulation of expression. In this regard, the gene may further comprise regulatory nucleic acids such as promoters, enhancers, termination and/or polyadenylation signals that are naturally associated with a given gene, or heterologous control signals. Genes may or may not be capable of being used to produce a functional protein. Genes can include both coding and non-coding regions.

As used herein, the terms "HPV E6" or "HPV E7" in the context of a nucleic acid or amino acid sequences, refers to a full or partial length HPV E6 or HPV E7 coding sequence, respectively, or a full or partial length HPV E6 or HPV E7 amino acid sequence, respectively (e.g., a full or partial length E6 gene of HPV strain HPV 16, genome strain NC 001526, a protein expression product thereof). In some embodiments, a synthetic coding sequence encodes at least about 30, 40, 50, 60, 70, 80, 90, 100, 120, 150, 200, 250, 300 or 350 contiguous amino acid residues, or almost up to the total number of amino acids present in a full-length HPV E6 or HPV E7 amino acid sequence (158 and 98 amino acid residues, respectively). In some embodiments, the synthetic coding sequence encodes a plurality of portions of the HPV E6 and/or HPV E7 polypeptides, wherein the portions are the same or different. In illustrative examples of this type, the synthetic coding sequence encodes a multi-epitope fusion protein. A number of factors can influence the choice of portion size. For example, the size of individual portions encoded by the synthetic coding sequence can be chosen such that it includes, or corresponds to the size of, T cell epitopes and/or B cell epitopes, and their processing requirements. Practitioners in the art will recognize that class I-restricted T cell epitopes are typically between 8 and 10 amino acid residues in length and if placed next to unnatural flanking residues, such epitopes can generally require 2 to 3 natural flanking amino acid residues to ensure that they are efficiently processed and presented. Class II-restricted T cell epitopes usually range between 12 and 25 amino acid residues in length and may not require natural flanking residues for efficient proteolytic processing although it is believed that natural flanking residues may play a role. Another important feature of class II-restricted epitopes is that they generally contain a core of 9-10 amino acid residues in the middle which bind specifically to class II MHC molecules with flanking sequences either side of this core stabilizing binding by associating with conserved structures on either side of class II MHC antigens in a sequence independent manner. Thus the functional region of class II-restricted epitopes is typically less than about 15 amino acid residues long. The size of linear B cell epitopes and the factors effecting their processing, like class II-restricted epitopes, are quite variable although such epitopes are frequently smaller in size than 15 amino acid residues. From the foregoing, it is advantageous, but not essential, that the size of individual portions of the HPV E6 and/or HPV E7 polypeptide is at least 6, 7, 8, 9, 10, 11, 12, 13, 14, 15, 20, 25, 30 amino acid residues. Suitably, the size of individual portions is no more than about 500, 200, 100, 80, 60, 50, 40 amino acid residues. In certain advantageous embodiments, the size of individual portions is sufficient for presentation by an antigen-presenting cell of a T cell and/or a B cell epitope contained within the peptide.

"Immune response" or "immunological response" refers to the concerted action of any one or more of lymphocytes, antigen-presenting cells, phagocytic cells, granulocytes, and soluble macromolecules produced by the above cells or the liver (including antibodies, cytokines, and complement) that results in selective damage to, destruction of, or elimination from the body of invading pathogens, cells or tissues infected with pathogens. In some embodiments, an "immune response" encompasses the development in an individual of a humoral and/or a cellular immune response to a polypeptide that is encoded by an introduced synthetic coding sequence of the invention. As known in the art, the terms "humoral immune response" includes and encompasses an immune response mediated by antibody molecules, while a "cellular immune response" includes and encompasses an immune response mediated by T-lymphocytes and/or other white blood cells. Hence, an immunological response may include one or more of the following effects: the production of antibodies by B-cells; and/or the activation of suppressor T-cells and/or memory/effector T-cells directed specifically to an antigen or antigens present in the composition or vaccine of interest. In some embodiments, these responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al., 1988, J Clin Microbiol. 26:231-235; Dreyer et al., 1999, AIDS Res Hum Retroviruses 15(17): 1563-1571). The innate immune system of mammals also recognizes and responds to molecular features of pathogenic organisms and cancer cells via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature dendritic cells of, for example, the monocyte and plasmacytoid lineage (MDC, PDC), as well as gamma, delta, alpha and beta T cells and B cells and the like. Thus, the present invention also contemplates an immune response wherein the immune response involves both an innate and adaptive response.

A composition is "immunogenic" if it is capable of either: a) generating an immune response against an HPV E6 or an HPV E7 polypeptide in an individual; or b) reconstituting, boosting, or maintaining an immune response in an individual beyond what would occur if the agent or composition was not administered. An agent or composition is immunogenic if it is capable of attaining either of these criteria when administered in single or multiple doses. The immune response may include a cellular immune response and/or humoral immune response in a subject.

By "immune response preference" is meant the preference with which an organism uses a codon to produce an immune response (for example a cellular immune response (e.g., a DTH response) and/or a humoral immune response). This preference can be evidenced, for example, by the level of immune response that is produced by a polynucleotide that comprises the codon in an open reading frame which codes for a polypeptide that produces the immune response. In certain embodiments, the preference of usage is independent of the route by which the polynucleotide is introduced into the subject. However, in other embodiments, the preference of usage is dependent on the route of introduction of the polynucleotide into the subject.

Throughout this specification, unless the context requires otherwise, the words "include," "includes" and "including" will be understood to imply the inclusion of a stated step or element or group of steps or elements but not the exclusion of any other step or element or group of steps or elements.

As used herein, the term "mammal" refers to any mammal including, without limitation, humans and other primates, including non-human primates such as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age. Thus, both adult and newborn individuals are intended to be covered.

The terms "operably connected," "operably linked" and the like as used herein refer to an arrangement of elements wherein the components so described are configured so as to perform their usual function. Thus, a given regulatory nucleic acid such as a promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence. Terms such as "operably connected," therefore, include placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a promoter with respect to a heterologous gene to be placed under its control is defined by the positioning of the promoter in its natural setting; i.e., the genes from which it is derived. Alternatively, "operably connecting" a HPV E6 or an HPV E7 coding sequence to a nucleic acid sequence that encodes a protein-destabilizing element (PDE) encompasses positioning and/or orientation of the E6 or E7 coding sequence relative to the PDE-encoding nucleic acid sequence so that (1) the coding sequence and the PDE-encoding nucleic acid sequence are transcribed together to form a single chimeric transcript and (2) the E6 or E7 coding sequence is 'in-frame' with the PDE-encoding nucleic acid sequence to produce a chimeric open reading frame comprising the E6 or E7 coding sequence and the PDE-encoding nucleic acid sequence.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

"Polypeptide," "peptide" and "protein" are used interchangeably herein to refer to a polymer of amino acid residues and to variants and synthetic analogues of the same. As used herein, the terms "polypeptide," "peptide" and "protein" are not limited to a minimum length of the product. Thus, peptides, oligopeptides, dimers, multimers, and the like, are included within the definition. Both full-length proteins and fragments thereof are encompassed by the definition. The terms also include post expression modifications of a polypeptide, for example, glycosylation, acetylation, phosphorylation and the like. In some embodiments, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

The terms "polypeptide variant," and "variant" refer to polypeptides that vary from a reference polypeptide by the addition, deletion or substitution (generally conservative in nature) of at least one amino acid residue. Typically, variants retain a desired activity of the reference polypeptide, such as antigenic activity in inducing an immune response against an HPV E6 or an HPV E7 polypeptide. In general, variant polypeptides are "substantially similar" or substantially identical" to the reference polypeptide, e.g., amino acid sequence identity or similarity of more than 50%, generally more than about 60%-70%, even more particularly about 80%-85% or more, such as at least about 90%-95% or more, when the two sequences are aligned. Often, the variants will include the same number of amino acids but will include substitutions, as explained herein.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for Windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in TABLES 3 and 4. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

The term "synthetic coding sequence" as used herein refers to a polynucleotide that is formed by recombinant or synthetic techniques and typically includes polynucleotides that are not normally found in nature.

The term "synonymous codon" as used herein refers to a codon having a different nucleotide sequence than another codon but encoding the same amino acid as that other codon.

"Treatment," "treat," "treated" and the like is meant to include both therapeutic and prophylactic treatment.

The term "ubiquitin molecule" refers to a member of the protein superfamily of ubiquitin-like proteins, which when conjugated to a target protein results in the introduction of that target protein into the cellular degradation machinery, including the proteasome.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

The terms "wild-type," with respect to an organism, polypeptide, or nucleic acid sequence, refer to an organism, polypeptide or nucleic acid sequence that is naturally occurring or available in at least one naturally occurring organism which is not changed, mutated, or otherwise manipulated by man.

2. Nucleic Acid Construct System

The present invention encompasses nucleotide constructs that comprise both a HPV E6 coding sequence, and a HPV E7 coding sequence, as described in detail, below.

2.1 HPV E6 Coding Sequences

The first and second synthetic coding sequences contemplated for use in the present invention encode proteinaceous molecules. Included within these coding sequences are polynucleotides that encode a HPV E6 polypeptide. Coding sequences encoding wild-type HPV E6 polypeptides are thus particularly suitable for use with the present invention, although variant HPV E6 polypeptides are also specifically contemplated. In accordance with the present invention, the HPV E6 polypeptides produced from the nucleic acid constructs of the present invention are encoded by codon-optimized coding sequences.

In some embodiments, a synthetic coding sequence is produced based on codon optimizing at least a portion of a wild-type HPV E6 coding sequence, an illustrative example of which includes the HPV type 16 E6 (Accession No. NC_001526.2):

[SEQ ID NO: 1]
ATGCACCAAAAGAGAACTGCAATGTTTCAGGACCCACAGGAGCGACCCAG

AAAGTTACCACAGTTATGCACAGAGCTGCAAACAACTATACATGATATAA

TATTAGAATGTGTGTACTGCAAGCAACAGTTACTGCGACGTGAGGTATAT

GACTTTGCTTTTCGGGATTTATGCATAGTATATAGAGATGGGAATCCATA

TGCTGTATGTGATAAATGTTTAAAGTTTTATTCTAAAATTAGTGAGTATA

GACATTATTGTTATAGTTTGTATGGAACAACATTAGAACAGCAATACAAC

AAACCGTTGTGTGATTTGTTAATTAGGTGTATTAACTGTCAAAAGCCACT

GTGTCCTGAAGAAAAGCAAAGACATCTGGACAAAAAGCAAAGATTCCATA

ATATAAGGGGTCGGTGGACCGGTCGATGTATGTCTTGTTGCAGATCATCA

AGAACACGTAGAGAAACCCAGCTGTAA.

Alternatively, an E6 coding sequence from any natural HPV variant is equally as applicable for use with the present invention. For example, an E6 nucleic acid sequence derived from any one of HPV type 18 (GenBank Accession No. KC662568.1), type 31 (GenBank Accession No. KC662562.1), type 33 (GenBank Accession No. KC662567.1) type 45 (GenBank Accession No. KC662572.1), or any other HPV type are specifically contemplated.

By way of an illustrative example, the polynucleotide sequence set forth in SEQ ID NO: 1 encodes the following amino acid sequence (UniProt Accession No. NP_041325):

[SEQ ID NO: 2]
MHQKRTAMFQDPQERPRKLPQLCTELQTTIHDIILECVYCKQQLLRREVY

DFAFRDLCIVYRDGNPYAVCDKCLKFYSKISEYRHYCYSLYGTTLEQQYN

KPLCDLLIRCINCQKPLCPEEKQRHLDKKQRFHNIRGRWTGRCMSCCRSS

RTRRETQL.

Also specifically contemplated for use with the present invention are mutant HPV E6 coding sequences. For example, single amino acid substitutions of the cysteine residue corresponding to position 70 in SEQ ID NO: 2, and the isoleucine residues corresponding to position 135 of SEQ ID NO: 2 are envisaged by the present inventors as being advantageous. Specifically, C70G and/or I135T variants of HPV E6 are contemplated for use with the present invention. These mutations are hypothesised by the present inventors as reducing the ability of E6 to degrade the tumour suppressor protein p53.

2.2 HPV E7 Coding Sequences

The first and second synthetic coding sequences contemplated for use in the present invention also encode HPV E7 polypeptides. Suitably, wild-type HPV E7 polypeptides can be codon-modified for use with the present invention, an illustrative example of which includes the HPV type 16 (strain NC_001526) E7 coding sequence, which has the following nucleotide sequence:

[SEQ ID NO: 3]
ATGCATGGAGATACACCTACATTGCATGAATATATGTTAGATTTGCAACC

AGAGACAACTGATCTCTACTGTTATGAGCAATTAAATGACAGCTCAGAGG

AGGAGGATGAAATAGATGGTCCAGCTGGACAAGCAGAACCGGACAGAGCC

CATTACAATATTGTAACCTTTTGTTGCAAGTGTGACTCTACGCTTCGGTT

GTGCGTACAAAGCACACACGTAGACATCCGTACGTTGGAAGACCTGTTAA

TGGGCACACTAGGAATTGTGTGCCCCATCTGTTCTCAGAAACCATAA (GenBank Accession No. KM058618).

The polynucleotide sequence set forth in SEQ ID NO: 3 encodes the following amino acid sequence (UniProt Accession No. P03129):

[SEQ ID NO: 4]
MFIGDTPTLHEYMLDLQPETTDLYCYEQLNDSSEEEDEIDGPAGQAEPDR

AHYNIVTFCCKCDSTLRLCVQSTHVDIRTLEDLLMGTLGIVCPICSQKP.

Similarly to what is described above in respect of HPV E6 coding sequences, an HPV E7 encoding nucleic acid sequence derived from any known HPV type is contemplated for use with the present invention (for example, HPV type 18 (GenBank accession no. KC662605.1 encoding the polypeptide identified by UniProt accession no. P03129), type 31 (GenBank accession no. KC662598.1encoding the E7 polypeptide identified by UniProt accession no. P17387), type 33 (GenBank accession no. KC662603.1 encoding the polypeptide identified by UniProt accession no. P06429), type 45 (GenBank accession no. KC662609.1 encoding the polypeptide identified by UniProt accession no. P21736), or any other HPV type are specifically contemplated).

Also specifically contemplated for use with the present invention are variant HPV E7 polypeptides. For example, mutations in the pRB1 binding domain (i.e., corresponding to amino acid residues 22 to 26 of the sequence set forth in SEQ ID NO: 4) are envisaged by the present inventors as being advantageous. Specifically, single amino acid variations of the cysteine residue corresponding to position 24 of SEQ ID NO: 4, or glutamic acid residue corresponding to position 26 of SEQ ID NO: 4 are specifically considered. More specifically, C24G and/or E26G variants of HPV E7 are contemplated for use with the present invention.

2.3 Ubiquitin Coding Sequence

In some embodiments broadly described above, the second construct of the construct system described above and elsewhere herein comprises a ubiquitin molecule. As such, the invention contemplates nucleic acid constructs that comprise a synthetic chimeric polynucleotide comprising a first nucleic acid sequence, which encodes a synthetic HPV E6-E7 fusion protein, and which is linked either downstream or upstream of, and in reading frame with, a second nucleic acid sequence encoding a ubiquitin molecule. In a preferred embodiment of this type, the second nucleic acid construct comprises a first nucleic acid sequence, encoding a synthetic HPV E6-E7 fusion protein, and which is linked immediately adjacent to, downstream of, and in reading frame with, a second nucleic acid sequence encoding a ubiquitin molecule. In another embodiment, the second polynucleotide comprises a first nucleic acid sequence, which encodes a synthetic HPV E6-E7 fusion protein, and which is linked upstream of, and in reading frame with, a second nucleic acid sequence encoding a ubiquitin molecule (or biologically active fragment thereof). In yet another embodiment of this type, the second polynucleotide comprises a first nucleic acid sequence, which encodes a synthetic HPV E6-E7 fusion protein, and which is linked immediately adjacent to, upstream of, and in reading frame with, a second nucleic acid sequence encoding a ubiquitin molecule.

Preferably, but not exclusively, the ubiquitin molecule coding sequence encodes a human ubiquitin B molecule and comprises, consists or consists essentially of at least a portion of the nucleic acid coding sequence forth in SEQ ID NO: 5 (corresponding to GenBank accession no. NM_018955), below:

[SEQ ID NO: 5]
ATGCAGATCTTCGTGAAAACCCTTACCGGCAAGACCATCACCCTTGAGGT

GGAGCCCAGTGACACCATCGAAAATGTGAAGGCCAAGATCCAGGATAAGG

AAGGCATTCCCCCCGACCAGCAGAGGCTCATCTTTGCAGGCAAGCAGCTG

GAAGATGGCCGTACTCTTTCTGACTACAACATCCAGAAGGAGTCGACCCT

GCACCTGGTCCTGCGTCTGAGAGGTGGTATGCAGATCTTCGTGAAGACCC

TGACCGGCAAGACCATCACCCTGGAAGTGGAGCCCAGTGACACCATCGAA

AATGTGAAGGCCAAGATCCAGGATAAAGAAGGCATCCCTCCCGACCAGCA

GAGGCTCATCTTTGCAGGCAAGCAGCTGGAAGATGGCCGCACTCTTTCTG

ACTACAACATCCAGAAGGAGTCGACCCTGCACCTGGTCCTGCGTCTGAGA

GGTGGTATGCAGATCTTCGTGAAGACCCTGACCGGCAAGACCATCACTCT

GGAGGTGGAGCCCAGTGACACCATCGAAAATGTGAAGGCCAAGATCCAAG

ATAAAGAAGGCATCCCCCCCGACCAGCAGAGGCTCATCTTTGCAGGCAAG

CAGCTGGAAGATGGCCGCACTCTTTCTGACTACAACATCCAGAAAGAGTC

GACCCTGCACCTGGTCCTGCGCCTGAGGGGTGGCTGTTAA.

In some preferred embodiments that ubiquitin coding sequences suitable for use with the present invention (such as that set forth in SEQ ID NO: 5), encode a single ubiquitin molecule, an example of which is set forth in SEQ ID NO: 6 (corresponding to cd01803):

[SEQ ID NO: 6]
MQIFVKTLTGKTITLEVEPSDTIENVKAKIQDKEGIPPDQQRLIFAGKQL

EDGRTLSDYNIQKESTLHLVLRLRGG.

As described above, biologically active fragments of ubiquitin molecules are also contemplated for use with the present invention. Specifically, the biologically active fragment of ubiquitin is such that when conjugated to a heterologous antigen (such as a synthetic HPV E6-E7 fusion protein) the rate of intracellular proteolytic degradation of the antigen is increased, enhanced or otherwise elevated relative to the antigen without the biological fragment of a ubiquitin polypeptide.

2.4 Codon Optimisation

In some embodiments, several codons within a parent (e.g., wild-type) HPV E7 coding sequence are mutated using the method described in the International Patent Publication No. WO 2009/049350. In brief, codons of the wild-type coding sequence are replaced with corresponding synonymous codons which are known to have a higher immune response preference than the codons they replace, as set out in TABLE 1.

Thus, it is within the realms of the present invention for around 5%, 10%, 15%, 20%, 25%, 30%, 35%, 40%, 45%, 50%, 55%, 60%, 65%, 70% 75% 80%, 85%, 90%, 91%, 92%, 93% 94%, 95%, 96%, 97%, 98%, 99%, or 100% of the nucleotides in the polynucleotide sequence to be synonymous codons as defined in TABLE 1.

In specific examples, the invention contemplates codon-optimizing coding sequences that encode amino acid sequences corresponding to at least a portion of wild-type HPV E6 or wild-type HPV E7 polypeptides. The sequences were codon optimised according to TABLE 1. By way of an illustrative example, all codons encoding an Ala amino acid can be replaced with a GCT codon; codons encoding an Arg amino acid can be replaced with any synonymous codon except from an AGG codon or a CGG codon; codons encoding a Asn amino acid can be replaced with a AAC codon; the majority of codons encoding an Asp amino acid can be changed to a GAC codon; the majority of codons encoding a Cys amino acid can be replaced with a TGC codon; a codon encoding a Glu amino acid may be replaced with GAA codons; codons encoding a Gly amino acid are replaced with a GGA codon; codons encoding an Ile amino acid can be replaced with an ATC codon; CTG and CTC codons were typically used to encode a Leu amino acid; codons encoding a Phe amino acid can be replaced with a TTT codon; codons encoding a Pro amino acid can be replaced with a CCC codon; the majority of codons encoding a Ser amino acid can be replaced with a TCG codon; the majority of codons encoding Thr can be replaced with a ACG codon; the majority of codons encoding a Tyr amino acid can be replaced with TAC; and valine-encoding codons GTA and GTT were replaced with GTC or GTG codons.

In some embodiments non-preferred codons are not substituted for codons that are more preferred. This is particularly the case when making a substitution that would result in a detrimental effect to the structure or function of the nucleic acid construct (for example, when the codon substitution is predicted to introduce a splice site, negatively affect mRNA stability/structure, or to introduce or disrupt an undesired or desired restriction enzyme site, and prevent the exhaustion of tRNA pools.

An illustrative example of a polynucleotide that accords with these embodiments is as follows:

```
HPV E6-E7 synthetic coding sequence -
                                          [SEQ ID NO: 7]
ATGGAAACGGACACGCTGCTGCTGTGGGTCCTGCTGCTGTGGGTCCCCGG

ATCGACGGGAGACGGATCGATGCACCAAAAGCGAACCGCTATGTTTCAGG

ACCCCCAGGAACGACCCCGTAAACTGCCCCAGCTCTGCACGGAACTGCAA

ACGACGATCCATGACATCATCCTCGAATGCGTGTACTGCAAGCAACAGCT

CCTGCGACGTGAAGTCTACGACTTTGCTTTTCGCGACCTGTGCATCGTCT

ACAGAGACGGAAACCCCTACGCTGTGGGAGACAAATGCCTGAAGTTTTAC

TCGAAAATCTCGGAATACCGCCACTACTGCTACTCGCTGTACGGAACCAC

GCTCGAACAGCAATACAACAAACCCTATGCGACCTGCTAATCCGCTGCA

TCAACTGCCAAAAGCCTCTCTGCCCTGAAGAAAAGCAACGCCATCTCGAC

AAAAAGCAAAGATTTCACAACACGCGTGGACGATGGACCGGACGATGCAT

GTCGTGCTGCAGATCGTCACGCACGCGTAGAGAAACCCAGCTGGCTGGAG

CTATGCATGGAGATACGCCTACGCTCCATGAATATATGCTCGATCTGCAA

CCCGAAACGACCGATCTCTACGGATATGGACAACTTAACGACTCGTCGGA

AGAAGAAGATGAAATCGATGGACCCGCTGGACAAGCTGAACCCGACCGTG

CTCATTACAACATCGTCACGTTTTGTTGCAAGTGTGACTCGACGCTGCGA

CTGTGCGTCCAATCGACCCACGTGGACATCCGTACGCTCGAAGACCTGCT

CATGGGAACGCTTGGAATCGTCTGCCCCATCTGCTCGCAGAAACCCTAA

Ubiquitinated HPV E6-E7 synthetic coding
sequence -
                                          [SEQ ID NO: 8]
ATGCAAATCTTTGTGAAGACGCTGACGGGAAAGACCATCACGCTCGAAGT

GGAACCCTCGGACACGATCGAAAACGTGAAAGCTAAGATCCAGGACAAGG

AAGGAATCCCCCCCGACCAGCAGAGACTGATCTTTGCTGGAAAGCAGCTC

GAAGACGGACGCACGCTGTCGGACTACAACATCCAGAAAGAATCGACGCT

CCACCTGGTCCTGAGACTCCGCGGAGCTATGCACCAAAAGCGAACCGCTA

TGTTTCAGGACCCCCAGGAACGACCCCGTAAACTGCCCCAGCTCTGCACG

GAACTGCAAACGACGATCCATGACATCATCCTCGAATGCGTGTACTGCAA

GCAACAGCTCCTGCGACGTGAAGTCTACGACTTTGCTTTTCGCGACCTGT

GCATCGTCTACAGAGACGGAAACCCCTACGCTGTGGGAGACAAATGCCTG

AAGTTTTACTCGAAAATCTCGGAATACCGCCACTACTGCTACTCGCTGTA

CGGAACCACGCTCGAACAGCAATACAACAAACCCTATGCGACCTGCTAA

TCCGCTGCATCAACTGCCAAAAGCCTCTCTGCCCTGAAGAAAAGCAACGC

CATCTCGACAAAAAGCAAAGATTTCACAACACGCGTGGACGATGGACCGG

ACGATGCATGTCGTGCTGCAGATCGTCACGCACGCGTAGAGAAACCCAGC

TGGCTGGAGCTATGCATGGAGATACGCCTACGCTCCATGAATATATGCTC

GATCTGCAACCCGAAACGACCGATCTCTACGGATATGGACAACTTAACGA

CTCGTCGGAAGAAGAAGATGAAATCGATGGACCCGCTGGACAAGCTGAAC

CCGACCGTGCTCATTACAACATCGTCACGTTTTGTTGCAAGTGTGACTCG

ACGCTGCGACTGTGCGTCCAATCGACCCACGTGGACATCCGTACGCTCGA

AGACCTGCTCATGGGAACGCTTGGAATCGTCTGCCCCATCTGCTCGCAGA

AACCCTAA
```

The parent HPV E6 or HPV E7 coding sequence that is codon-optimized to make the synthetic coding sequence is suitably a wild-type or natural gene. However, it is possible that the parent HPV E6 or HPV E7 coding sequence is not naturally-occurring but has been engineered using recombinant techniques. Wild-type polynucleotides can be obtained from any suitable source, such as from eukaryotic or prokaryotic organisms, including but not limited to mammals or other animals, and pathogenic organisms such as yeasts, bacteria, protozoa and viruses.

As will be appreciated by those of skill in the art, it is generally not necessary to immunize with a synthetic coding sequence encoding a polypeptide that shares exactly the same amino acid sequence with an HPV E6 and/or HPV E7 polypeptide to produce an immune response to that antigen. In some embodiments, therefore, the synthetic HPV fusion proteins encoded by the synthetic coding sequence is a variant of at least a portion of an HPV E6 and HPV E7 polypeptide. "Variant" polypeptides include proteins derived from the HPV E6 or HPV E7 polypeptide by deletion (so-called truncation) or addition of one or more amino acids to the N-terminal and/or C-terminal end of the HPV E6 or HPV E7 polypeptide; deletion or addition of one or more amino acids at one or more sites in the HPV E6 or HPV E7 polypeptide; or substitution of one or more amino acids at one or more sites in the HPV E6 or HPV E7 polypeptide. Variant polypeptides encompassed by the present invention will have at least about 40%, 50%, 60%, 70%, generally at least 75%, 80%, 85%, typically at least about 90% to 95% or more, and more typically at least about 96%, 97%, 98%, 99% or more sequence similarity or identity with the amino acid sequence of a wild-type HPV E6 or HPV E7 polypeptide or portion thereof as determined by sequence alignment programs described elsewhere herein using default parameters. A variant of an HPV E6 or HPV E7 polypeptide may differ from the wild-type sequence generally by as much as 100, 50 or 20 amino acid residues or suitably by as few as 1-15 amino acid residues, as few as 1-10, such as 6-10, as few as 5, as few as 4, 3, 2, or even 1 amino acid residue.

3. Construction of Synthetic HPV E6-E7 Fusion Proteins

Suitably, the synthetic HPV E6-E7 fusion proteins that are encoded by the construct systems of the present invention as described above and elsewhere herein, often comprise a polypeptide linker sequence located between and contiguous with the HPV E6 and HPV E7 polypeptide sequences.

In some embodiments, the linker sequence comprises one or more glycine residues. In some of the same and other embodiments, the linker sequence comprises one or more alanine residues. Suitable linker polypeptides are well known in the art. Although any linker is equally suitable for use with the present invention, some non-limiting illustrative examples of suitable linker sequences are Ala-Gly-Ala, Gly-Ser, (Gly-Ser)$_2$, (Gly-Ser)$_3$, Gly$_2$-Ser-Gly, (Gly$_2$-Ser-Gly)$_2$, (Gly$_2$-Ser-Gly)$_3$, Gly$_3$-Ser-Gly, (Gly$_3$-Ser-Gly)$_2$, (Gly$_3$-Ser-Gly)$_3$, Gly$_4$-Ser, (Gly$_4$-Ser)$_2$, and (Gly$_4$-Ser)$_3$.

Variant polypeptide sequences of the synthetic HPV E6-E7 fusion proteins may contain conservative amino acid substitutions at various locations along their sequence, as compared to the wild-type HPV E6 or HPV E7 polypeptide sequences.

A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., 1992, *Science* 256(5062): 1430-1445), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic. Dependent on their structural properties, amino acid residues may fall in two or more classes. For the naturally-occurring protein amino acids, sub-classification according to the this scheme is presented in TABLE 3.

TABLE 3

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Conservative substitutions are shown in TABLE 4 below under the heading of exemplary substitutions. More preferred substitutions are shown under the heading of preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 4

EXEMPLARY AND PREFERRED AMINO ACID SUBSTITUTIONS

| Original Residue | Exemplary Substitutions | Preferred Substitutions |
|---|---|---|
| Ala | Gly, Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly, Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., Biochemistry, third edition, Wm.C. Brown Publishers (1993).

3.1 Methods of Substituting Codons

Replacement of one codon for another can be achieved using standard methods known in the art. For example, codon modification of a parent polynucleotide can be effected using several known mutagenesis techniques including, for example, oligonucleotide-directed mutagenesis, mutagenesis with degenerate oligonucleotides, and region-specific mutagenesis. Exemplary in vitro mutagenesis techniques are described for example in U.S. Pat. Nos. 4,184,917, 4,321,365 and 4,351,901 or in the relevant sections of Ausubel, et al. (CURRENT PROTOCOLS IN MOLECULAR BIOLOGY, John Wiley & Sons, Inc. 1997) and of Sambrook, et al., (MOLECULAR CLONING. A LABORATORY MANUAL, Cold Spring Harbor Press, 1989). Instead of in vitro mutagenesis, the synthetic coding sequence can be synthesized de novo using readily available machinery as described, for example, in U.S. Pat. No. 4,293,652. However, it should be noted that the present invention is not dependent on, and not directed to, any one particular technique for constructing the synthetic coding sequence.

3.2 Regulatory Nucleic Acids

The first and second constructs typically each comprise a synthetic coding sequence that is operably linked to a regulatory nucleic acid. The regulatory nucleic acid suitably comprises transcriptional and/or translational control sequences, which will be compatible for expression in the organism of interest or in cells of that organism. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the organism of interest or may be derived from an alternative source, where the region is functional in the chosen organism. The choice of promoter will differ depending on the intended host or cell or tissue type. For example, promoters which could be used for expression in mammals include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, the mouse mammary tumor virus LTR promoter, the adenovirus major late promoter (Ad MLP), the herpes simplex virus promoter, and a HPV promoter, particularly the HPV upstream regulatory region (URR), among others. All these promoters are well described and readily available in the art.

Enhancer elements may also be used herein to increase expression levels of the mammalian constructs. Examples include the SV40 early gene enhancer, as described for example in Dijkema et al. (1985, EMBO J. 4:761), the enhancer/promoter derived from the long terminal repeat (LTR) of the Rous Sarcoma Virus, as described for example in Gorman et al. (1982, Proc. Natl. Acad. Sci. USA 79:6777), and elements derived from human CMV, as described for example in Boshart et al. (1985, Cell 41:521), such as elements included in the CMV intron A sequence.

The first and second constructs may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

In some embodiments, the first and second constructs further contain a selectable marker gene to permit selection of cells containing the construct. Selection genes are well known in the art and will be compatible for expression in the cell of interest.

It will be understood, however, that expression of protein-encoding polynucleotides in heterologous systems is now well known, and the present invention is not necessarily directed to or dependent on any particular vector, transcriptional control sequence or technique for expression of the polynucleotides. Rather, synthetic coding sequences prepared according to the methods set forth herein may be introduced into a mammal in any suitable manner in the form of any suitable construct or vector, and the synthetic coding sequences may be expressed with known transcription regulatory elements in any conventional manner.

Furthermore, the first and second constructs can be constructed to include chimeric antigen-coding gene sequences, encoding, e.g., multiple antigens/epitopes of interest, for example derived from a single or from more than one HPV E6 or HPV E7 polypeptide. In certain embodiments, multi-cistronic cassettes (e.g., bi-cistronic cassettes) can be constructed allowing expression of multiple adjuvants and/or antigenic polypeptides from a single mRNA using, for example, the EMCV IRES, or the like. In other embodiments, adjuvants and/or antigenic polypeptides can be encoded on separate coding sequences that are operably connected to independent transcription regulatory elements.

3.3 Vectors

The first and second constructs described above are suitably in the form of a vector that is suitable for expression of recombinant proteins in mammalian cells, and particularly those identified for the induction of neutralizing immune responses by genetic immunization. Vectors prepared specifically for use in DNA vaccines generally combine a eukaryotic region that directs expression of the transgene in the target organism with a bacterial region that provides selection and propagation in the *Escherichia coli* (*E. coli*) host. The eukaryotic region contains a promoter upstream, and a polyadenylation signal (polyA) downstream, of the gene of interest. Upon transfection into the cell nucleus, the promoter directs transcription of an mRNA that includes the transgene. The polyadenylation signal mediates mRNA cleavage and polyadenylation, which leads to efficient mRNA export to the cytoplasm. A Kozak sequence (gccgccRccATGG consensus, transgene ATG start codon within the Kozak sequence is underlined, critical residues in caps, R=A or G) is often included. The Kozak sequence is recognized in the cytoplasm by ribosomes and directs efficient transgene translation. The constitutive human Cytomegalovirus (CMV) promoter is the most common promoter used in DNA vaccines since it is highly active in most mammalian cells transcribing higher levels of mRNA than alternative viral or cellular promoters. PolyA signals are typically used to increase polyadenylation efficiency resulting in increased mRNA levels, and improved transgene expression.

3.4 Viral Vectors

In some embodiments, the first and second constructs of the invention are in the form of expression vectors which are suitably selected from self-replicating extra-chromosomal vectors (e.g., plasmids) and vectors that integrate into a host genome. In illustrative examples of this type, the expression vectors are viral vectors, such as simian virus 40 (SV40) or bovine papilloma virus (BPV), which has the ability to replicate as extra-chromosomal elements (Eukaryotic Viral Vectors, Cold Spring Harbor Laboratory, Gluzman ed., 1982; Sarver et al., 1981, *Mol. Cell. Biol.* 1:486) or alphavirus self amplifying vectors (Geall et al 2012). Viral vectors include retroviral (lentivirus), adeno-associated virus (see, e.g., Okada, 1996, *Gene Ther.* 3:957-964; Muzyczka, 1994, *J. Clin. Invst.* 94:1351; U.S. Pat. Nos. 6,156,303; 6,143,548 5,952,221, describing AAV vectors; see also U.S. Pat. Nos. 6,004,799; 5,833,993), adenovirus (see, e.g., U.S. Pat. Nos. 6,140,087; 6,136,594; 6,133,028; 6,120,764), reovirus, herpesvirus, rotavirus genomes etc., modified for introducing and directing expression of a polynucleotide or transgene in cells. Retroviral vectors can include those based upon murine leukaemia virus (see, e.g., U.S. Pat. No. 6,132,731), gibbon ape leukaemia virus (see, e.g., U.S. Pat. No. 6,033,905), simian immuno-deficiency virus, human immuno-deficiency virus (see, e.g., U.S. Pat. No. 5,985,641), and combinations thereof.

Vectors also include those that efficiently deliver genes to animal cells in vivo (e.g., stem cells) (see, e.g., U.S. Pat. Nos. 5,821,235 and 5,786,340; Croyle et al., 1998, *Gene Ther.* 5:645; Croyle et al., 1998, Pharm. Res. 15:1348; Croyle et al., 1998, *Hum. Gene Ther.* 9:561; Foreman et al., 1998, *Hum. Gene Ther.* 9:1313; Wirtz et al., 1999, *Gut* 44:800). Adenoviral and adeno-associated viral vectors suitable for in vivo delivery are described, for example, in U.S. Pat. Nos. 5,700,470, 5,731,172 and 5,604,090. Additional vectors suitable for in vivo delivery include herpes simplex virus vectors (see, e.g., U.S. Pat. No. 5,501,979), retroviral vectors (see, e.g., U.S. Pat. Nos. 5,624,820, 5,693,508 and 5,674,703; and WO92/05266 and WO92/14829), bovine papilloma virus (BPV) vectors (see, e.g., U.S. Pat. No. 5,719,054), CMV-based vectors (see, e.g., U.S. Pat. No. 5,561,063) and parvovirus, rotavirus and Norwalk virus vectors. Lentiviral vectors are useful for infecting dividing as well as non-dividing cells (see, e.g., U.S. Pat. No. 6,013,516).

Additional viral vectors which will find use for delivering the nucleic acid molecules encoding the antigens of interest include those derived from the pox family of viruses, including vaccinia virus and avian poxvirus. By way of example, vaccinia virus recombinants expressing the first and second constructs can be constructed as follows. The antigen coding sequence is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with. respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the first and second constructs of the present invention. For a description of Sindbis-virus derived vectors useful for the practice of the instant methods, see, Dubensky et al. (1996, *J. Virol.* 70:508-519; and International Publication Nos. WO 95/07995, WO 96/17072); as well as, Dubensky, Jr., T. W., et al., U.S. Pat. No. 5,843,723, and Dubensky, Jr., T. W., U.S. Pat. No. 5,789,245. Exemplary vectors of this type are chimeric alphavirus vectors comprised of sequences derived from Sindbis virus and Venezuelan equine encephalitis virus. See, e.g., Perri et al. (2003, *J. Virol.* 77: 10394-10403) and International Publication Nos. WO 02/099035, WO 02/080982, WO 01/81609, and WO 00/61772.

In other illustrative embodiments, lentiviral vectors are employed to deliver the first and second constructs of the invention into selected cells or tissues. Typically, these vectors comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). A wide variety of lentiviruses may be utilized within the context of the present invention, including for example, lentiviruses selected from the group consisting of HIV, HIV-1, HIV-2, FIV, BIV, EIAV, MVV, CAEV, and SIV. Illustrative examples of lentiviral vectors are described in PCT Publication Nos. WO 00/66759, WO 00/00600, WO 99/24465, WO 98/51810, WO 99/51754, WO 99/31251, WO 99/30742, and WO 99/15641. Desirably, a third generation SIN lentivirus is used. Commercial suppliers of third generation SIN (self-inactivating) lentiviruses include Invitrogen (ViraPower Lentiviral Expression System). Detailed methods for construction, transfection, harvesting, and use of lentiviral vectors are given, for example, in the Invitrogen technical manual "ViraPower Lentiviral Expression System version B 050102 25-0501" (available at http://www.invitrogen.com/Content/Tech-Online/molecular_biology/manuals_p-ps/virapower_lentiviral_system_man.pdf). Lentiviral vectors have emerged as an efficient method for gene transfer. Improvements in biosafety characteristics have made these vectors suitable for use at biosafety level 2 (BL2). A number of safety features are incorporated into third generation SIN (self-inactivating) vectors. Deletion of the viral 3' LTR U3 region results in a provirus that is unable to transcribe a full length viral RNA. In addition, a number of essential genes are provided in trans, yielding a viral stock that is capable of but a single round of infection and integration. Lentiviral vectors have several advantages, including: 1) pseudotyping of the vector using amphotropic envelope proteins allows them to infect virtually any cell type; 2) gene delivery to quiescent, post mitotic, differentiated cells, including neurons, has been demonstrated; 3) their low cellular toxicity is unique among transgene delivery systems; 4) viral integration into the genome permits long term transgene expression; 5) their packaging capacity (6-14 kb) is much larger than other retroviral, or adeno-associated viral vectors. In a recent demonstration of the capabilities of this system, lentiviral vectors expressing GFP were used to infect murine stem cells resulting in live progeny, germline transmission, and promoter-, and tissue-specific expression of the reporter (Ailles, L. E. and Naldini, L., HIV-1-Derived Lentiviral Vectors. In: Trono, D. (Ed.), Lentiviral Vectors, Springer-Verlag, Berlin, Heidelberg, N.Y., 2002, pp. 31-52). An example of the current generation vectors is outlined in FIG. 2 of a review by Lois et al. (2002, *Science*, 295 868-872).

The first and second constructs can also be delivered without a vector. For example, the constructs can be packaged as DNA or RNA in liposomes or lipid nanoparticles prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA: micromoles lipid), or more of lipid. For a review of the use of liposomes as carriers for delivery of nucleic acids, see, Hug and Sleight, (1991, *Biochim. Biophys. Acta.* 1097: 1-17); and Straubinger et al., in *Methods of Enzymology* (1983), 101: 512-527.

In other embodiments, the first and second constructs comprise, consist or consist essentially of an mRNA coding sequence comprising a synthetic HPV E6-E7 fusion protein coding sequence. The synthetic HPV E6-E7 fusion protein coding sequence may optionally comprise a Kozak sequence and/or a polyadenylated sequence, as described above. Suitably, the first and second constructs optionally further comprise chemical modification to the RNA structure as known in the art, such as phosphorothioation of the backbone or 2'-methoxyethylation (2'MOE) of ribose sugar groups to enhance uptake, stability, and ultimate effectiveness of the mRNA coding sequence (see, Agrawal 1999; Gearry et al., 2001).

3.5 Minicircle Vectors

In some embodiments, the first and/or second constructs are in the form of minicircle vectors. A minicircle vector is a small, double stranded circular DNA molecule that provides for persistent, high level expression of a synthetic HPV E6-E7 fusion protein coding sequence that is present on the vector, which sequence of interest may encode a polypeptide (e.g., synthetic HPV E6-E7 fusion protein). The synthetic HPV E6-E7 fusion protein coding sequence is operably linked to regulatory sequences present on the minicircle vector, which regulatory sequences control its expression. Suitable minicircle vectors for use with the present invention are described, for example, in published U.S. Patent Application No. 2004/0214329, and can be prepared by the method described in Darquet et al., Gene Ther. (1997) 4: 1341-1349. In brief, a synthetic HPV E6-E7 fusion protein coding sequence is flanked by attachment sites for a recombinase, which is expressed in an inducible fashion in a portion of the vector sequence outside of the coding sequence.

In brief, minicircle vectors can be prepared with plasmids similar to pBAD.phi.C31.hFIX and pBAD.phi.C31.RHB and used to transform *E. coli*. Recombinases known in the art, for example, lambda and cre, are suitable for incorporation to the minicircle vectors. The expression cassettes present in the minicircle vectors may contain sites for transcription initiation and termination, as well as a ribosome binding site in the transcribed region, for translation. The minicircle vectors may include at least one selectable marker, for example, dihydrofolate reductase, G418, or a marker of neomycin resistance for eukaryotic cell culture; and tetracycline, kanamycin, or ampicillin resistance genes for culturing in *E. coli* and other prokaryotic cell culture. The minicircle producing plasmids may include at least one origin of replication to allow for the multiplication of the vector in a suitable eukaryotic or a prokaryotic host cell. Origins of replication are known in the art, as described, for example, in Genes II, Lewin, B., ed., John Wiley & Sons, New York (1985).

3.6 Mammalian Expression Vectors

In some embodiments, the vector comprises a first or second synthetic coding sequence without any additional and/or non-functional sequences, (e.g., cryptic ORFs that may be expressed in the subject). This is especially beneficial within the transcribed UTRs to prevent production of vector encoded cryptic peptides in a subject that may induce undesirable adaptive immune responses. Illustrative examples of vectors that are suitable for use with the present invention include NTC8485 and NCT8685 (Nature Technology Corporation, Nebraska, USA). Alternatively, the parent vector, NTC7485, can be used. NTC7485 was designed to comply with the U.S. Food and Drug Administration (FDA) regulatory guidance regarding DNA vaccine vector compositions (FDA 1996, FDA 2007, and reviewed in Williams et al, 2009). Specifically, all sequences that are not essential for *Escherichia coli* plasmid replication or mammalian cell expression of the target gene were eliminated. Synthetic eukaryotic mRNA leader and terminator sequences were utilized in the vector design to limit DNA sequence homology with the human genome in order to reduce the possibility of chromosomal integration.

In other embodiments, the vector may comprise a nucleic acid sequence encoding an ancillary functional sequence (e.g., a sequence effecting transport or post translational sequence modification of the synthetic HPV E6-E7 fusion protein, non-limiting examples of which include a signal or targeting sequence). For example, NTC8482 targets encoded protein into the secretory pathway using an optimized tissue plasminogen activator (TPA) signal peptide.

In some embodiments, expression of the synthetic HPV E6-E7 fusion protein is driven from an optimized chimeric promoter-intron (e.g., SV40-CMV-HTLV-1 R synthetic intron). In one aspect of these embodiments, the vectors encode a consensus Kozak translation initiation sequence and an ATG start codon. Notably, the chimeric cytomegalovirus (CMV) promoter achieves significantly higher expression levels than traditional human CMV promoter-based vectors (Luke et al, 2009).

In one embodiment, the DNA plasmid is cloned into the NTC8485, NTC8685, or NTC9385R vector families, which combine minimal prokaryotic sequences and include an antibiotic free sucrose selectable marker. These families also contain a novel chimeric promoter that directs superior mammalian cell expression (see, Luke et al., 2009; Luke et al, 2011; and Williams, 2013).

3.7 Antibiotic-Free Selection Using RNA Selection Markers

As described above, in some embodiments, the vector is free of any non-essential sequences for expressing the synthetic constructs of the invention, for example, an antibiotic resistance marker. Kanamycin resistance (KanR) is the most utilized resistance gene in vectors to allow selective retention of plasmid DNA during bacterial fermentation. However, to ensure safety regulatory agencies generally recommend elimination of antibiotic-resistance markers from therapeutic and vaccine plasmid DNA vectors. The presence of an antibiotic resistance gene in the vaccine vector is therefore considered undesirable by regulatory agencies, due to the potential transfer of antibiotic resistance to endogenous microbial flora and the potential activation and transcription of the genes from mammalian promoters after cellular incorporation into the genome. Vectors that are retrofit to replace the KanR marker with short RNA antibiotic-free markers generally have the unexpected benefit of improved expression. The NTC7485 vector comprises a kanamycin resistance antibiotic selection marker.

In some embodiments, selection techniques other than antibiotic resistance are used. By way of an illustrative example, the NTC8485, NTC8684 and NTC9385R vectors are derived from the NTC7485 vector, wherein the KanR antibiotic selection marker is replaced with a sucrose selectable RNA-OUT marker. Accordingly, in some embodiments, the vaccine vector comprises an antibiotic-free selection system. Although a number of antibiotic-free plasmid retention systems have been developed in which the vector-encoded selection marker is not protein based, superior expression and manufacture has been observed with SNA vaccine vectors that incorporate RNA based antibiotic-free selection markers.

An illustrative example of a suitable RNA based antibiotic-free selection system is the sucrose selection vector, RNA-OUT, a small 70 bp antisense RNA system (Nature Technology Corporation, Nebraska, USA); pFAR4 and pCOR vectors encode a nonsense suppressor tRNA marker; and the pMINI vector utilizes the ColE1 origin-encoded RNAI antisense RNA. Each of these plasmid-borne RNAs regulate the translation of a host chromosome encoded selectable marker allowing plasmid selection. For example, RNA-OUT represses expression of a counter-selectable marker (SacB) from the host chromosome (selection host DH5α att$_\lambda$::P$_{5/66/6}$-RNA-IN-SacB, catR). SacB encodes a levansucrase, which is toxic in the presence of sucrose. Plasmid selection is achieved in the presence of sucrose. Moreover, for both RNA-OUT vectors and pMINI, high yielding fermentation processes have been developed. In all these vectors, replacement of the KanR antibiotic selection marker results has previously been demonstrated to improve transgene expression in the target organism, showing that elimination of antibiotic selection to meet regulatory criteria may unexpectedly also improve vector performance.

4. Compositions

The invention also provides compositions, particularly immunogenic compositions, comprising the first and second constructs described herein which may be delivered, for example, using the same or different vectors or vehicles. The first and second constructs may be administered separately, concurrently or sequentially. The immunogenic compositions may be given more than once (e.g., a "prime" administration followed by one or more "boosts") to achieve the desired effects. The same composition can be administered in one or more priming and one or more boosting steps. Alternatively, different compositions can be used for priming and boosting.

4.1 Pharmaceutically Acceptable Components

The compositions of the present invention are suitably pharmaceutical compositions. The pharmaceutical compositions often comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) *Remington: The Science and Practice of Pharmacy.* 20th ed., ISBN: 0683306472.

The pharmaceutical compositions may include various salts, excipients, delivery vehicles and/or auxiliary agents as are disclosed, e.g., in U.S. patent application Publication No. 2002/0019358, published Feb. 14, 2002.

Alternatively or in addition, the pharmaceutical compositions of the present invention may include one or more transfection facilitating compounds that facilitate delivery of polynucleotides to the interior of a cell, and/or to a desired location within a cell. As used herein, the terms "transfection facilitating compound," "transfection facilitating agent," and "transfection facilitating material" are synonymous, and may be used interchangeably. It should be noted that certain transfection facilitating compounds may also be "adjuvants" as described infra, i.e., in addition to facilitating delivery of polynucleotides to the interior of a cell, the compound acts to alter or increase the immune response to the antigen encoded by that polynucleotide. Examples of the transfection facilitating compounds include, but are not limited to, inorganic materials such as calcium phosphate, alum (aluminium phosphate), zinc and gold particles (e.g., "powder" type delivery vehicles); peptides that are, for example, canonic, intercell targeting (for selective delivery to certain cell types), intracell targeting (for nuclear localization or endosomal escape), and amphipathic (helix forming or pore forming); proteins that are, for example, basic (e.g., positively charged) such as histones, targeting (e.g., asialoprotein), viral (e.g., Sendai virus coat protein), and pore-forming; lipids that are, for example, cationic (e.g., DMRIE, DOSPA, DC-Chol), basic (e.g., steryl amine), neutral (e.g., cholesterol), anionic (e.g., phosphatidyl serine), and zwitterionic (e.g., DOPE, DOPC); cationic polymers such as chitosans (eg. Richardson et al 1999; Köping-Höggård et al 2001) and polymers such as dendrimers, star-polymers, "homogenous" poly-amino acids (e.g., poly-lysine, poly-arginine), "heterogeneous" poly-amino acids (e.g., mixtures of lysine & glycine), co-polymers, polyvinylpyrrolidinone (PVP), poloxamers (e.g. CRL 1005) and polyethylene glycol (PEG). A transfection facilitating material can be used alone or in combination with one or more other transfection facilitating materials. Two or more transfection facilitating materials can be combined by chemical bonding (e.g., covalent and ionic such as in lipidated polylysine, PEGylated polylysine) (Toncheva, et al., *Biochim. Biophys. Acta* 1380(3): 354-368 (1988)), mechanical mixing (e.g., tree moving materials in liquid or solid phase such as "polylysine+cationic lipids") (Gao and Huang, *Biochemistry* 35: 1027-1036 (1996); Trubetskoy, et al., *Biochem. Biophys. Acta* 1131: 311-313 (1992)), and aggregation (e.g., co-precipitation, gel forming such as in cationic lipids+polylactide, and polylysine+gelatin).

One category of transfection facilitating materials is cationic lipids. Examples of cationic lipids are 5-carboxyspermylglycine dioctadecylamide (DOGS) and dipalmitoyl-phosphatidylethanolamine-5-carboxyspermylamide (DPPES). Cationic cholesterol derivatives are also useful, including {3β-[N—N',N'-dimethylamino)ethane]-carbomoyl}-cholesterol (DC-Chol). Dimethyldioctdecyl-ammonium bromide (DDAB), N-(3-aminopropyl)-N,N-(bis-(2-tetradecyloxyethyl))-N-methyl-ammonium bromide (PA-DEMO), N-(3-aminopropyl)-N,N-(bis-(2-dodecyloxyethyl))-N-methyl-ammonium bromide (PA-DELO), N,N,N-tris-(2-dodecyloxy)ethyl-N-(3-amino)propyl-ammonium bromide (PA-TELO), and N1-(3-aminopropyl)((2-dodecyloxy)ethyl)-N2-(2-dodecyloxy)ethyl-1-piperazinaminium bromide (GA-LOE-BP) can also be employed in the present invention.

Non-diether cationic lipids, such as DL-1,2-doleoyl-3-dimethylaminopropyl-β-hydroxyethylammonium (DORI diester), 1-O-oleyl-2-oleoyl-3-dimethylaminopropyl-p-hydroxyethylammonium (DORI ester/ether), and their salts promote in vivo gene delivery. In some embodiments, cationic lipids comprise groups attached via a heteroatom attached to the quaternary ammonium moiety in the head group. A glycyl spacer can connect the linker to the hydroxyl group.

Specific, but non-limiting cationic lipids for use in certain embodiments of the present invention include DMRIE ((±)-N-(2-hydroxyethyl)-N,N-dimethyl-2,3-bis(tetradecyloxy)-1-propanaminium bromide), GAP-DMORIE ((±)-N-(3-aminopropyl)-N,N-dimethyl-2,3-bis(syn-9-tetradecenyloxy)-1-propanaminium bromide), and GAP-DMRIE((±)-N-(3-aminopropyl)-N,N-dimethyl-2,3-(bis-dodecyloxy)-1-propaniminium bromide).

Other specific but non-limiting cationic surfactants for use in certain embodiments of the present invention include Bn-DHRIE, DhxRIE, DhxRIE-OAc, DhxRIE-OBz and Pr-DOctRIE-OAc. These lipids are disclosed in copending U.S. patent application Ser. No. 10/725,015. In another aspect of the present invention, the cationic surfactant is Pr-DOctRIE-OAc.

Other cationic lipids include (±)-N,N-dimethyl-N-[2-(sperminecarboxamido)ethyl]-2,3-bis(dioleyloxy)-1-propaniminium pentahydrochloride (DOSPA), (±)-N-(2-aminoethyl)-N,N-dimethyl-2,3-bis(tetradecyloxy)-1-propaniminium bromide (β-aminoethyl-DMRIE or βAE-DMRIE) (Wheeler, et al., Biochim. Biophys. Acta 1280:1-11 (1996), and (±)-N-(3-aminopropyl)-N,N-dimethyl-2,3-bis(dodecyloxy)-1-propaniminium bromide (GAP-DLRIE) (Wheeler, et al., Proc. Natl. Acad. Sci. USA 93:11454-11459 (1996)), which have been developed from DMRIE.

Other examples of DMRIE-derived cationic lipids that are useful for the present invention are (±)-N-(3-aminopropyl)-N,N-dimethyl-2,3-(bis-decyloxy)-1-propanaminium bromide (GAP-DDRIE), (±)-N-(3-aminopropyl)-N,N-dimethyl-2,3-(bis-tetradecyloxy)-1-propanaminium bromide (GAP-DMRIE), (±)-N-((N"-methyl)-N'-ureyl)propyl-N,N-dimethyl-2,3-bis(tetradecyloxy-)-1-propanaminium bromide (GMU-DMRIE), (±)-N-(2-hydroxyethyl)-N,N-dimethyl-2,3-bis(dodecyloxy)-1-propananninium bromide (DLRIE), and (±)-N-(2-hydroxyethyl)-N,N-dimethyl-2,3-bis-([Z]-9-octadecenyloxy)propyl-1-propaniminium bromide (HP-DORIE).

In the embodiments where the immunogenic composition comprises a cationic lipid, the cationic lipid may be mixed with one or more co-lipids. For purposes of definition, the term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films. One non-limiting class of co-lipids are the zwitterionic phospholipids, which include the phosphatidylethanolamines and the phosphatidylcholines. Examples of phosphatidylethanolamines, include DOPE, DMPE and DPyPE. In certain embodiments, the co-lipid is DPyPE which comprises two phytanoyl substituents incorporated into the diacylphosphatidylethanolamine skeleton and the cationic lipid is GAP-DMORIE, (resulting in VAXFECTIN adjuvant). In other embodiments, the co-lipid is DOPE, the CAS name is 1,2-diolyeoyl-sn-glycero-3-phosphoethanolamine.

When a composition of the present invention comprises a cationic lipid and co-lipid, the cationic lipid:co-lipid molar ratio may be from about 9:1 to about 1:9, from about 4:1 to about 1:4, from about 2:1 to about 1:2, or about 1:1.

In order to maximize homogeneity, the cationic lipid and co-lipid components may be dissolved in a solvent such as chloroform, followed by evaporation of the cationic lipid/co-lipid solution under vacuum to dryness as a film on the inner surface of a glass vessel (e.g., a Rotovap round-bottomed flask). Upon suspension in an aqueous solvent, the amphipathic lipid component molecules self-assemble into homogenous lipid vesicles. These lipid vesicles may subsequently be processed to have a selected mean diameter of uniform size prior to complexing with, for example, a codon-optimized polynucleotide of the present invention, according to methods known to those skilled in the art. For example, the sonication of a lipid solution is described in Feigner et al., *Proc. Natl. Acad. Sci. USA* 8: 7413-7417 (1987) and in U.S. Pat. No. 5,264,618.

In those embodiments where the composition includes a cationic lipid, polynucleotides of the present invention are complexed with lipids by mixing, for example, a plasmid in aqueous solution and a solution of cationic lipid:co-lipid as prepared herein are mixed. The concentration of each of the constituent solutions can be adjusted prior to mixing such that the desired final plasmid/cationic lipid:co-lipid ratio and the desired plasmid final concentration will be obtained upon mixing the two solutions. The cationic lipid:co-lipid mixtures are suitably prepared by hydrating a thin film of the mixed lipid materials in an appropriate volume of aqueous solvent by vortex mixing at ambient temperatures for about 1 minute. The thin films are prepared by admixing chloroform solutions of the individual components to afford a desired molar solute ratio followed by aliquoting the desired volume of the solutions into a suitable container. The solvent is removed by evaporation, first with a stream of dry, inert gas (e.g. argon) followed by high vacuum treatment.

Other hydrophobic and amphiphilic additives, such as, for example, sterols, fatty acids, gangliosides, glycolipids, lipopeptides, liposaccharides, neobees, niosomes, prostaglandins and sphingolipids, may also be included in compositions of the present invention. In such compositions, these additives may be included in an amount between about 0.1 mol % and about 99.9 mol % (relative to total lipid), about 1-50 mol %, or about 2-25 mol %.

The first and second constructs may also be encapsulated, adsorbed to, or associated with, particulate carriers. Such carriers present multiple copies of selected constructs to the immune system. The particles can be taken up by professional antigen presenting cells such as macrophages and dendritic cells, and/or can enhance antigen presentation through other mechanisms such as stimulation of cytokine release. Examples of particulate carriers include those derived from polymethyl methacrylate polymers, as well as microparticles derived from poly(lactides) and poly(lactide-co-glycolides), known as PLG. See, e.g., Jeffery et al., 1993, *Pharm. Res.* 10: 362-368; McGee J. P., et al., 1997, *J Microencapsul.* 14(2): 197-210; O'Hagan D. T., et al., 1993, *Vaccine* 11(2): 149-54.

Furthermore, other particulate systems and polymers can be used for the in vivo delivery of the compositions described herein. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminium silicates including bentonite and kaolin, chromic oxide, magnesium silicate, talc, and the like, will find use with the present methods. See, e.g., Feigner, P. L., *Advanced Drug Delivery Reviews* (1990) 5: 163-187, for a review of delivery systems useful for gene transfer. Peptoids (Zuckerman, R. N., et al., U.S. Pat. No. 5,831,005, issued Nov. 3, 1998) may also be used for delivery of a construct of the present invention.

Additional embodiments of the present invention are drawn to compositions comprising an auxiliary agent which is administered before, after, or concurrently with the synthetic constructs. As used herein, an "auxiliary agent" is a substance included in a composition for its ability to enhance, relative to a composition which is identical except for the inclusion of the auxiliary agent, the entry of polynucleotides into vertebrate cells in vivo, and/or the in vivo expression of polypeptides encoded by such polynucleotides. Certain auxiliary agents may, in addition to enhancing entry of polynucleotides into cells, enhance an immune response to an immunogen encoded by the polynucleotide. Auxiliary agents of the present invention include nonionic, anionic, cationic, or zwitterionic surfactants or detergents, with nonionic surfactants or detergents being preferred, chelators, DNase inhibitors, poloxamers, agents that aggregate or condense nucleic acids, emulsifying or solubilizing agents, wetting agents, gel-forming agents, and buffers.

Auxiliary agents for use in compositions of the present invention include, but are not limited to non-ionic detergents and surfactants IGEPAL CA 6300 octylphenyl-polyethylene glycol, NONIDET NP-40 nonylphenoxypolyethoxyethanol, NONIDET P-40 octylphenoxypolyethoxyethanol, TWEEN-20 polysorbate 20, TWEEN-80 polysorbate 80, PLURONIC F68 poloxamer (ave. MW: 8400; approx. MW of hydrophobe, 1800; approx. wt. % of hydrophile, 80%), PLURONIC F77 poloxamer (ave. MW: 6600; approx. MW of hydrophobe, 2100; approx. wt. % of hydrophile, 70%), PLURONIC P65 poloxamer (ave. MW: 3400; approx. MW of hydrophobe, 1800; approx. wt. % of hydrophile, 50%), TRITON X-100 4-(1,1,3,3-tetramethylbutyl)phenyl-polyethylene glycol, and TRITON X-114 (1,1,3,3-tetramethylbutyl)phenyl-polyethylene glycol; the anionic detergent sodium dodecyl sulfate (SDS); the sugar stachyose; the condensing agent DMSO; and the chelator/DNAse inhibitor EDTA, CRL 1005 (12 kpa, 5% POE), and BAK (Benzalkonium chloride 50% solution, available from Ruger Chemical Co. Inc.). In certain specific embodiments, the auxiliary agent is DMSO, NONIDET P-40 octylphenoxypolyethoxyethanol, PLURONIC F68 poloxamer (ave. MW: 8400; approx. MW of hydrophobe, 1800; approx. wt. % of hydrophile, 80%), PLURONIC F77 poloxamer (ave. MW: 6600; approx. MW of hydrophobe, 2100; approx. wt. % of hydrophile, 70%), PLURONIC P65 (ave. MW: 3400; approx. MW of hydrophobe, 1800; approx. wt. % of hydrophile, 50%), Pluronic PLURONIC L64 poloxamer (ave. MW: 2900; approx. MW of hydrophobe, 1800; approx. wt. % of hydrophile, 40%), and PLURONIC F108 poloxamer (ave. MW: 14600; approx. MW of hydrophobe, 3000; approx. wt. % of hydrophile, 80%). See, e.g., U.S. patent application Publication No. 2002/0019358, published Feb. 14, 2002.

Certain compositions of the present invention can further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant," can be a transfection facilitating material. Similarly, certain "transfection facilitating materials" described supra, may also be an "adjuvant." An adjuvant maybe used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminium-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: inert carriers, such as alum, bentonite, latex, and acrylic particles; PLURONIC block polymers, such as TITERMAX (block copolymer CRL-8941, squalene (a metabolizable oil) and a microparticulate silica stabilizer); depot formers, such as Freunds adjuvant, surface active materials, such as saponin, lysolecithin, retinal, Quil A, liposomes, and PLURONIC polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly(oxypropylene) tri-block copolymers. Also included as adjuvants are transfection-facilitating materials, such as those described above.

Poloxamers which may be screened for their ability to enhance the immune response according to the present invention include, but are not limited to, commercially available poloxamers such as PLURONIC surfactants, which are block copolymers of propylene oxide and ethylene oxide in which the propylene oxide block is sandwiched between two ethylene oxide blocks. Examples of PLURONIC surfactants include PLURONIC L121 poloxamer (ave. MW: 4400; approx. MW of hydrophobe, 3600; approx. wt % of hydrophile, 10%), PLURONIC L101 poloxamer (ave. MW: 3800; approx. MW of hydrophobe, 3000; approx. wt. % of hydrophile, 10%), PLURONIC L81 poloxamer (ave. MW: 2750; approx. MW of hydrophobe, 2400; approx. wt. % of hydrophile, 10%), PLURONIC L61 poloxamer (ave. MW: 2000; approx. MW of hydrophobe, 1800; approx. wt. % of hydrophile, 10%), PLURONIC L31 poloxamer (ave. MW: 1100; approx. MW of hydrophobe, 900; approx. wt. % of hydrophile, 10%), PLURONIC L122 poloxamer (ave. MW: 5000; approx. MW of hydrophobe, 3600; approx. wt. % of hydrophile, 20%), PLURONIC L92 poloxamer (ave. MW: 3650; approx. MW of hydrophobe, 2700; approx. wt. % of hydrophile, 20%), PLURONIC L72 poloxamer (ave. MW: 2750; approx. MW of hydrophobe, 2100; approx. wt. % of hydrophile, 20%), PLURONIC L62 poloxamer (ave. MW: 2500; approx. MW of hydrophobe, 1800; approx. wt. % of hydrophile, 20%), PLURONIC L42 poloxamer (ave. MW: 1630; approx. MW of hydrophobe, 1200; approx. wt. % of hydrophile, 20%), PLURONIC L63 poloxamer (ave. MW: 2650; approx. MW of hydrophobe, 1800; approx. wt. % of hydrophile, 30%), PLURONIC L43 poloxamer (ave. MW: 1850; approx. MW of hydrophobe, 1200; approx. wt. % of hydrophile, 30%), PLURONIC L64 poloxamer (ave. MW: 2900; approx. MW of hydrophobe, 1800; approx. wt. % of hydrophile, 40%), PLURONIC L44 poloxamer (ave. MW: 2200; approx. MW of hydrophobe, 1200; approx. wt. % of hydrophile, 40%), PLURONIC L35 poloxamer (ave. MW: 1900; approx. MW of hydrophobe, 900; approx. wt. % of hydrophile, 50%), PLURONIC P123 poloxamer (ave. MW: 5750; approx. MW of hydrophobe, 3600; approx. wt. % of hydrophile, 30%), PLURONIC P103 poloxamer (ave. MW: 4950; approx. MW of hydrophobe, 3000; approx. wt. % of hydrophile, 30%), PLURONIC P104 poloxamer (ave. MW: 5900; approx. MW of hydrophobe, 3000; approx. wt. % of hydrophile, 40%), PLURONIC P84 poloxamer (ave. MW: 4200; approx. MW of hydrophobe, 2400; approx. wt. % of hydrophile, 40%), PLURONIC P105 poloxamer (ave. MW: 6500; approx. MW of hydrophobe, 3000; approx. wt. % of hydrophile, 50%), PLURONIC P85 poloxamer (ave. MW: 4600; approx. MW of hydrophobe, 2400; approx. wt. % of hydrophile, 50%), PLURONIC P75 poloxamer (ave. MW: 4150; approx. MW of hydrophobe, 2100; approx. wt. % of hydrophile, 50%), PLURONIC P65 poloxamer (ave. MW: 3400; approx. MW of hydrophobe, 1800; approx. wt. % of hydrophile, 50%), PLURONIC F127 poloxamer (ave. MW: 12600; approx. MW of hydrophobe, 3600; approx. wt. % of hydrophile, 70%), PLURONIC F98 poloxamer (ave. MW: 13000; approx. MW of hydrophobe, 2700; approx. wt. % of hydrophile, 80%), PLURONIC F87 poloxamer (ave. MW: 7700; approx. MW of hydrophobe, 2400; approx. wt. % of hydrophile, 70%), PLURONIC F77 poloxamer (ave. MW: 6600; approx. MW of hydrophobe, 2100; approx. wt. % of hydrophile, 70%), PLURONIC F108 poloxamer (ave. MW: 14600; approx. MW of hydrophobe, 3000; approx. wt. % of hydrophile, 80%), PLURONIC F98 poloxamer (ave. MW: 13000; approx. MW of hydrophobe, 2700; approx. wt. % of hydrophile, 80%), PLURONIC F88 poloxamer (ave. MW: 11400; approx. MW of hydrophobe, 2400; approx. wt. % of hydrophile, 80%), PLURONIC F68 poloxamer (ave. MW: 8400; approx. MW of hydrophobe, 1800; approx. wt. % of hydrophile, 80%), PLURONIC F38 poloxamer (ave. MW: 4700; approx. MW of hydrophobe, 900; approx. wt. % of hydrophile, 80%).

Reverse poloxamers which may be screened for their ability to enhance the immune response according to the present invention include, but are not limited to PLURONIC R 31R1 reverse poloxamer (ave. MW: 3250; approx. MW of hydrophobe, 3100; approx. wt. % of hydrophile, 10%), PLURONIC R25R1 reverse poloxamer (ave. MW: 2700; approx. MW of hydrophobe, 2500; approx. wt. % of hydrophile, 10%), PLURONIC R 17R1 reverse poloxamer (ave. MW: 1900; approx. MW of hydrophobe, 1700; approx. wt.

% of hydrophile, 10%), PLURONIC R 31R2 reverse poloxamer (ave. MW: 3300; approx. MW of hydrophobe, 3100; approx. wt. % of hydrophile, 20%), PLURONIC R 25R2 reverse poloxamer (ave. MW: 3100; approx. MW of hydrophobe, 2500; approx. wt. % of hydrophile, 20%), PLURONIC R 17R2 reverse poloxamer (ave. MW: 2150; approx. MW of hydrophobe, 1700; approx. wt. % of hydrophile, 20%), PLURONIC R 12R3 reverse poloxamer (ave. MW: 1800; approx. MW of hydrophobe, 1200; approx. wt. % of hydrophile, 30%), PLURONIC R 31R4 reverse poloxamer (ave. MW: 4150; approx. MW of hydrophobe, 3100; approx. wt. % of hydrophile, 40%), PLURONIC R 25R4 reverse poloxamer (ave. MW: 3600; approx. MW of hydrophobe, 2500; approx. wt. % of hydrophile, 40%), PLURONIC R 22R4 reverse poloxamer (ave. MW: 3350; approx. MW of hydrophobe, 2200; approx. wt. % of hydrophile, 40%), PLURONIC R17R4 reverse poloxamer (ave. MW: 3650; approx. MW of hydrophobe, 1700; approx. wt. % of hydrophile, 40%), PLURONIC R 25R5 reverse poloxamer (ave. MW: 4320; approx. MW of hydrophobe, 2500; approx. wt. % of hydrophile, 50%), PLURONIC R10R5 reverse poloxamer (ave. MW: 1950; approx. MW of hydrophobe, 1000; approx. wt. % of hydrophile, 50%), PLURONIC R 25R8 reverse poloxamer (ave. MW: 8550; approx. MW of hydrophobe, 2500; approx. wt. % of hydrophile, 80%), PLURONIC R 17R8 reverse poloxamer (ave. MW: 7000; approx. MW of hydrophobe, 1700; approx. wt. % of hydrophile, 80%), and PLURONIC R 10R8 reverse poloxamer (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymers of polyethylene and polypropylene glycol such as SYNPERONIC L121 (ave. MW: 4400), SYNPERONIC L122 (ave. MW: 5000), SYNPERONIC P104 (ave. MW: 5850), SYNPERONIC P105 (ave. MW: 6500), SYNPERONIC P123 (ave. MW: 5750), SYNPERONIC P85 (ave. MW: 4600) and SYNPERONIC P94 (ave. MW: 4600), in which L indicates that the surfactants are liquids, P that they are pastes, the first digit is a measure of the molecular weight of the polypropylene portion of the surfactant and the last digit of the number, multiplied by 10, gives the percent ethylene oxide content of the surfactant; and compounds that are nonylphenyl polyethylene glycol such as SYNPERONIC NP10 (nonylphenol ethoxylated surfactant-10% solution), SYNPERONIC NP30 (condensate of 1 mole of nonylphenol with 30 moles of ethylene oxide) and SYNPERONIC NP5 (condensate of 1 mole of nonylphenol with 5.5 moles of naphthalene oxide).

Other poloxamers which may be screened for their ability to enhance the immune response according to the present invention include: (a) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—R0, wherein R0 is a straight chain aliphatic group of 2 to 6 carbon atoms, which may be substituted, wherein said polyether segments comprise at least one of an A-type of B-type segment. See U.S. Pat. No. 5,656,611. Other poloxamers of interest include CRL1005 (12 kDa, 5% POE), CRL8300 (11 kDa, 5% POE), CRL2690 (12 kDa, 10% POE), CRL4505 (15 kDa, 5% POE) and CRL1415 (9 kDa, 10% POE).

Other auxiliary agents which may be screened for their ability to enhance the immune response according to the present invention include, but are not limited to, Acacia (gum arabic); the poloxyethylene ether R—O—(C2H4O)x-H (BRIJ), e.g., polyethylene glycol dodecyl ether (BRIJ 35, x=23), polyethylene glycol dodecyl ether (BRIJ 30, x=4), polyethylene glycol hexadecyl ether (BRIJ 52 x=2), polyethylene glycol hexadecyl ether (BRIJ 56, x=10), polyethylene glycol hexadecyl ether (BRIJ 58P, x=20), polyethylene glycol octadecyl ether (BRIJ 72, x=2), polyethylene glycol octadecyl ether (BRIJ 76, x=10), polyethylene glycol octadecyl ether (BRIJ® 78P, x=20), polyethylene glycol oleyl ether (BRIJ 92V, x=2), and polyoxyl 10 oleyl ether (BRIJ 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40); octylphenoxypolyethoxyethanol (NONIDET NP-40 from Amresco); ethyl phenol poly (ethylene glycol ether)n, n=1 1 (NONIDET P40 from Roche); octyl phenol ethylene oxide condensate with about 9 ethylene oxide units (NONIDET P40); IGEPAL CA 630 ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20; polyoxyethylene sorbitan monooleate (polysorbate 80, or TWEEN-80); propylene glycol diacetate; propylene glycol monstearate; protamine sulfate; proteolytic enzymes; sodium dodecyl sulfate (SDS); sodium monolaurate; sodium stearate; sorbitan derivatives (SPAN), e.g., sorbitan monopalmitate (SPAN 40), sorbitan monostearate (SPAN 60), sorbitan tristearate (SPAN 65), sorbitan monooleate (SPAN 80), and sorbitan trioleate (SPAN 85); 2,6,10,15,19,23-hexamethyl-2,6,10,14,18,22-tetracosa-hexaene (squalene); stachyose; stearic acid; sucrose; surfactin (lipopeptide antibiotic from *Bacillus subtilis*); dodecylpoly(ethyleneglycolether)9 (THESIT) MW 582.9; octyl phenol ethylene oxide condensate with about 9-10 ethylene oxide units (TRITON X-100); octyl phenol ethylene oxide condensate with about 7-8 ethylene oxide units (TRITON X-114); tris(2-hydroxyethyl)amine (trolamine); and emulsifying wax.

In certain adjuvant compositions, the adjuvant is a cytokine. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNΩ), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and M3P-1 beta), *Leishmania* elongation initiating factor (LEIF), and Flt-3 ligand.

In certain compositions of the present invention, the polynucleotide construct may be complexed with an adjuvant composition comprising (±)-N-(3-aminopropyl)-N,N-dimethyl-2,3-bis(syn-9-tetradeceneyloxy)-1-propan-aminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising GAP-DMORIE and DPyPE at a 1:1 molar ratio is referred to herein as VAXFECTIN adjuvant. See, e.g., PCT Publication No. WO 00/57917.

In other embodiments, the polynucleotide itself may function as an adjuvant as is the case when the polynucleotides of the invention are derived, in whole or in part, from bacterial DNA. Bacterial DNA containing motifs of unmethylated CpG-dinucleotides (CpG-DNA) triggers innate immune cells in vertebrates through a pattern recognition receptor (including toll receptors such as TLR 9) and thus possesses potent immunostimulatory effects on macrophages, dendritic cells and B-lymphocytes. See, e.g., Wagner, H., *Curr. Opin. Microbiol.* 5: 62-69 (2002); Jung, J. et al., *J. Immunol.* 169: 2368-73 (2002); see also Klinman, D. M. et al., *Proc. Natl Acad. Sci. U.S.A.* 93: 2879-83 (1996). Methods of using unmethylated CpG-dinucleotides as adjuvants are described in, for example, U.S. Pat. Nos. 6,207,646, 6,406,705 and 6,429,199.

The ability of an adjuvant to increase the immune response to an antigen is typically manifested by a significant increase in immune-mediated protection. For example, an increase in humoral immunity is typically manifested by a significant increase in the titre of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Nucleic acid molecules and/or polynucleotides of the present invention, e.g., plasmid DNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a human.

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995). Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims.

4.2 Dosage

The present invention is generally concerned with therapeutic compositions, i.e., to treat disease after infection. The compositions will comprise a "therapeutically effective amount" of the compositions defined herein, such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

For example, after around 24 hours of administering the pharmaceutical compositions described herein, a dose-dependent immune response occurs in human subjects receiving a dose of at least about 30 μg, 40 μg, 50 μg, 75 μg, 80 μg, 85 μg, 90 μg, 95 μg, 100 μg, 200 μg, 250 μg, 300 μg, 400 μg, 500 μg, 600 μg, 700 μg, 800 μg, 900 μg, 1000 μg, more than 1 mg, or any integer in between. If suitable, doses can be administered in more than one unit (e.g., 1 mg can be divided into two units each comprising 500 μg doses).

Dosage treatment may be a single dose schedule or a multiple dose schedule. In some embodiments, a dose of between around 30 μg to around 1 mg or above is sufficient to induce an immune response to the composition. Thus, the methods of the present invention include dosages of the compositions defined herein of around 30 μg, 100 μg, 300 μg, 1 mg, or more, in order to treat HPV infection.

The compositions of the present invention can be suitably formulated for injection. The composition may be prepared in unit dosage form in ampoules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampoules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The container in which the polynucleotide is packaged is labeled, and the label bears a notice in the form prescribed by a governmental agency, for example the U.S. Food and Drug Administration, which notice is reflective of approval by the agency under Federal law, of the manufacture, use, or sale of the polynucleotide material therein for human administration.

In most countries, federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. §§ 301-392. Regulation for biologic material, comprising products made from the tissues of animals is provided under 42 U.S.C. § 262. Similar approval is required by most foreign countries. Regulations vary from country to country, but the individual procedures are well known to those in the art.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs.

In preferred protocols, a formulation comprising the naked polynucleotide in an aqueous carrier is injected into tissue in amounts of from 10 µl per site to about 1 ml per site. The concentration of polynucleotide in the formulation is from about 0.1 µg/ml to about 20 mg/ml.

4.3 Routes of Administration

Once formulated, the compositions of the invention can be administered directly to the subject (e.g., as described above). Direct delivery of first and second construct-containing compositions in vivo will generally be accomplished with or without vectors, as described above, by injection using either a conventional syringe, needleless devices such as BIOJECT™ or a gene gun, such as the ACCELL™ gene delivery system (PowderMed Ltd, Oxford, England) or microneedle device. The constructs can be delivered (e.g., injected) intradermally. Delivery of nucleic acid into cells of the epidermis is particularly preferred as this mode of administration provides access to skin-associated lymphoid cells and provides for a transient presence of nucleic acid (e.g., DNA) in the recipient.

Suitably, the compositions described herein are formulated on a patch for microneedle administration.

In other embodiments the compositions of the invention are administered by electroporation. Such techniques greatly increase plasmid transfer across the cell plasma membrane barrier to directly or indirectly transfect plasmid into the cell cytoplasm.

Additionally, biolistic delivery systems employing particulate carriers such as gold and tungsten, are especially useful for delivering the compositions of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefor, see, e.g., U.S. Pat. Nos. 4,945,050; 5,036,006; 5,100,792; 5,179,022; 5,371,015; and 5,478,744. In illustrative examples, gas-driven particle acceleration can be achieved with devices such as those manufactured by PowderMed Pharmaceuticals PLC (Oxford, UK) and PowderMed Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest. Other devices and methods that may be useful for gas-driven needle-less injection of compositions of the present invention include those provided by BIOJECT, Inc. (Portland, Oreg.), some examples of which are described in U.S. Pat. Nos. 4,790,824; 5,064,413; 5,312,335; 5,383,851; 5,399,163; 5,520,639 and 5,993,412.

Alternatively, micro-cannula- and microneedle-based devices (such as those being developed by Becton Dickinson and others) can be used to administer the compositions of the invention. Illustrative devices of this type are described in EP 1 092 444 A1, and U.S. application Ser. No. 606,909, filed Jun. 29, 2000. Standard steel cannula can also be used for intra-dermal delivery using devices and methods as described in U.S. Ser. No. 417,671, filed Oct. 14, 1999. These methods and devices include the delivery of substances through narrow gauge (about 30 G) "micro-cannula" with limited depth of penetration, as defined by the total length of the cannula or the total length of the cannula that is exposed beyond a depth-limiting feature. It is within the scope of the present invention that targeted delivery of substances including the compositions described herein can be achieved either through a single microcannula or an array of microcannula (or "microneedles"), for example 3-6 microneedles mounted on an injection device that may include or be attached to a reservoir in which the substance to be administered is contained.

5. Kits

Any of the compositions or components described herein may be comprised in a kit. In non-limiting examples, materials and reagents required for detecting and/or treating a HPV infection in a subject as described herein may be assembled together in a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried powder. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that facilitate isolation of the labeled lectin probes. It may also include components that preserve or maintain the lectin probes or that protect against their degradation. Such kits generally will comprise, in suitable means, distinct containers for each individual reagent or solution.

A kit will generally also include instructions for employing the kit components as well the use of any other reagent not included in the kit. Instructions may include variations that can be implemented.

Kits of the invention may also include one or more of the following: Control glycospecies; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

In order that the invention may be readily understood and put into practical effect, particular preferred embodiments will now be described by way of the following non-limiting examples.

EXAMPLES

Example 1

Comparison of Immune Response Elicited by Polynucleotide Constructs Encoding E6-E6 Fusion Protein and E6 and E7 Polypeptides Separately The polynucleotide construct system is composed of two polynucleotide constructs: NTC8485-O-U-E6[C70G, I135T]-AGA-E7[C24G, E26G] and NTC-O-s-E6[C70G, I135T]-AGA-E7[C24G, E26G]. These constructs encode ubiquitinated and secreted forms of a mutant HPV16 E6-E7 fusion protein, respectively.

Mice were immunized as described below with either 10 µg of the E6-E7 fusion protein-encoding construct system, or 30 µg of E6 polypeptide-encoding construct or E7 polypeptide-encoding construct. Two injections were administered, the first on day 0 and the second on day 21.

Figure 2:
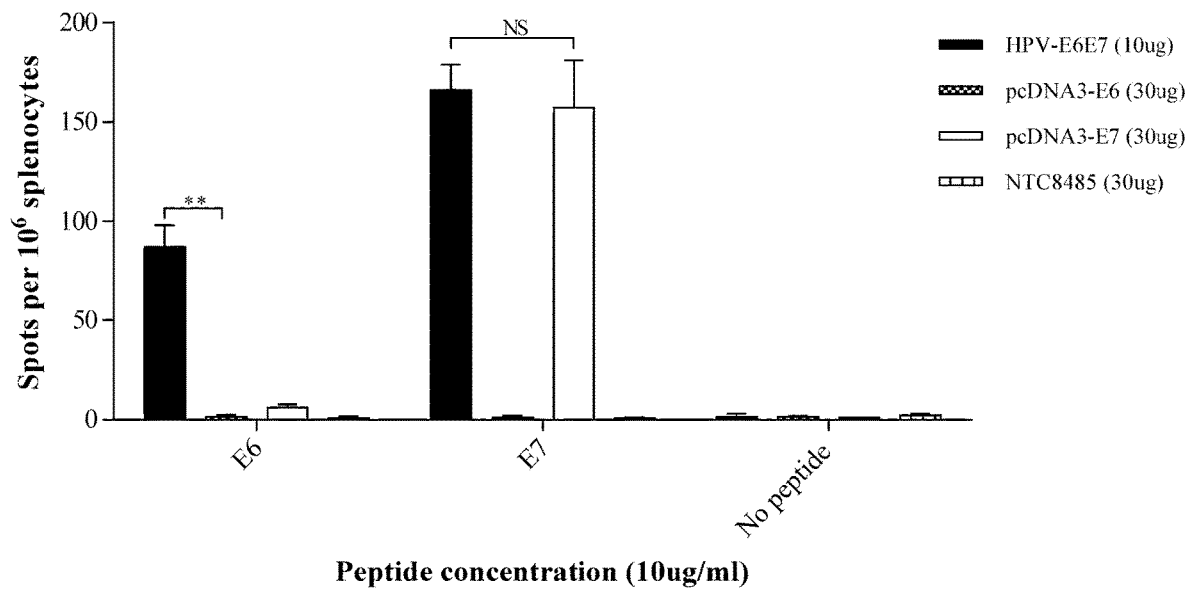
FIG. 2 shows cellular immune responses elicited by exposure to an E6 peptide antigen or an E7 peptide antigen measured by ELISPOT. Mice were immunized with either the sE6[C70G, I135T]-AGA-E7[C24G, E26G]/Ubi-E6 [C70G, I135T]-AGA-E7[C24G, E26G] ("E6E7") polynucleotide construct system (10 μg), an E6-encoding polynucleotide (30 μg) or an E7-encoding polynucleotide (30 μg). Immunization of mice with the E6E7 polynucleotide construct system elicited a substantial cellular immune response to both E6 and E7 antigenic peptides, whereas the E6 immunized mice failed to elicit any significant cellular immune response to any antigenic polypeptides. ** indicates P<0.001 and NS indicates not statistically significant, as determined by unpaired two-tailed t-test. Means from one representative repeat using pooled spleens from 5 mice are plotted. The error bars indicate the SEM of triplicate wells.
Figure 3:
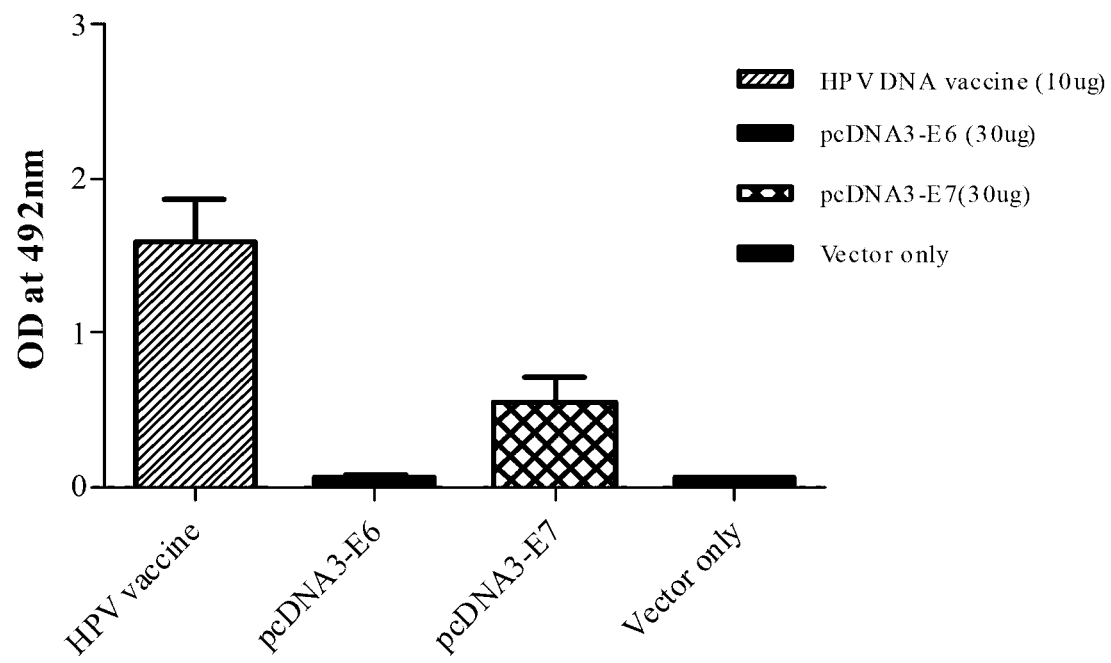
FIG. 3 shows a graphical representation of the results of an ELISA measuring the anti-E7 antibody immune response induced by immunization of mice with E6 and E7 polynucleotides. Mice were immunized with either the sE6 [C70G, I135T]-AGA-E7[C24G, E26G]/Ubi-E6[C70G, I135T]-AGA-E7[C24G, E26G] ("E6E7") polynucleotide construct system (10 µg), an E6-encoding polynucleotide (30 µg) or an E7-encoding polynucleotide (30 µg). Immunization with the E6E7 polynucleotide construct system elicited a greater immune response to E7 antigenic peptides than the E7 alone polynucleotide construct. The results in this figure are from one representative repeat. Error bars indicate the SEM.

FIGS. 2 and 3 show that immunization with the combined construct system elicits a significant cellular immune response to E6 and E7 (FIG. 2) and a strong antibody response to E7 (FIG. 3). The strong cellular response is particularly surprising as no cellular immune response was elicited in mice immunized with an E6 polynucleotide construct alone (see FIG. 2). Furthermore, although there is no statistical difference between the cellular immune response elicited in mice immunized with the E6E7 construct system as compared to mice immunized with the E7 polynucleotide construct alone, the E6-E7 polynucleotide construct was administered at one third of the dose (i.e., 10 µg of the E6-E7 polynucleotide construct system was administered, whereas 30 µg of the E7 polynucleotide construct was administered). Accordingly, FIG. 2 clearly demonstrate the E6-E7 polynucleotide construct system has a much greater efficacy than each of the polynucleotide sequences alone.

FIG. 3 clearly shows that the anti-E7 antibody response elicited by mice immunized with the E6-E7 polynucleotide construct system is significantly greater than that elicited by mice immunized with the E7 polynucleotide construct alone. As expected, immunisation with the E6 construct alone did not give rise to measurable levels of anti-E7 antibody.

Materials and Methods

Plasmid Preparation

The inserts for the HPV DNA vaccine constructs were designed based on a wild type HPV type 16 sequence (Genbank accession number NC_001526). Mutations were introduced into the coding sequences for E6 and E7 to render the proteins non-transforming and sequence encoding an Ala-Gly-Ala linker was added.

Sequences encoding either a single ubiquitin repeat or an Igk secretory signal peptide were added upstream of and in-frame with the E6/E7 coding sequence to make constructs encoding ubiquitinated or secreted forms of the fusion protein, respectively. Kozak sequences were also introduced.

The codons were modified according to Admedus Vaccine's codon optimisation protocol (described above in section 2.4). The sequences were checked to avoid internal splice sites and the unintended introduction of restriction enzyme sites that might interfere with cloning.

To further increase the safety of the vaccine, the E6 and E7 coding sequences were modified such that they should result in the production of an E6-E7 fusion protein. The was done in an effort to reduce the oncogenic potential of these polypeptide sequences. This involved removing the stop codon from the E6 gene sequence and inserting sequence encoding an Ala-Gly-Ala linker between the modified E6 and E7 sequences. While codon modification was used to enhance expression of the construct, it should also limit the possibility of recombination of the vaccine sequences with wild-type HPV viruses. The sequence was checked for splice sites to reduce the likelihood of splice variants being produced.

The desired sequences were sent to GeneArt (Life Technologies) for synthesis and cloning into pcDNA3.1 vector. The inserts were then subcloned into the NTC8485 vector to generate NTC8485-O-Ubi-E6[C70G, I135T]-AGA-E7 [C24G, E26G] (as set forth in SEQ ID NO: 9, shown below) and NTC8485-O-s-E6[C70G, I135T]-AGA-E7[C24G, E26G] (as set forth in SEQ ID NO: 10, shown below) (NTC8485 vectors are from Nature Technology Corporation and are shown in FIG. 1).

NTC8485-O-s-E6[C70G, I135T]-AGA-E7[C24G, E26G]

(SEQ ID NO: 9)

```
GCTAGCCCGCCTAATGAGCGGGCTTTTTTTTCTTAGGCTGCCTCGCGCGTTTCGGTGATGACGGTGAAAACC
TCTGACACATGCAGCTCCCGGAGACGGTCACAGCTTGTCTGTAAGCGGATGCCGGGAGCAGACAAGCCCGTC
AGGGCGCGTCAGCGGGTGTTGGCGGGTGTCGGGGCGCAGCCATGACCCAGTCACGTAGCGATAGCGGAGTGT
ATACTGGCTTAACTATGCGGCATCAGAGCAGATTGTACTGAGAGTGCACCATATGCGGTGTGAAATACCGCA
CAGATGCGTAAGGAGAAAATACCGCATCAGGCGCTCTTCCGCTTCCTCGCTCACTGACTCGCTGCGCTCGGT
CGTTCGGCTGCGGCGAGCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAGGCCGCGTTGCTGGCGTT
TTTCCATAGGCTCCGCCCCCTGACGAGCATCACAAAAATCGACGCTCAAGTCAGAGGTGGCGAAACCCGAC
AGGACTATAAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTAAAAATGAAGTTTTAA
ATCAATCTAAAGTATATATGAGTAAACTTGGTCTGACAGTTACCAATGCTTAATCAGTGAGGCACCTATCTC
AGCGATCTGTCTATTTCGTTCATCCATAGTTGCCTGACTCCTGCAAACCACGTTGTGGTAGAATTGGTAAAG
AGAGTCGTGTAAAATATCGAGTTCGCACATCTTGTTGTCTGATTATTGATTTTTGGCGAAACCATTTGATCA
TATGACAAGATGTGTATCTACCTTAACTTAATGATTTTGATAAAAATCATTAGGTACCCCTGATCACTGTGG
AATGTGTGTCAGTTAGGGTGTGGAAAGTCCCCAGGCTCCCCAGCAGGCAGAAGTATGCAAAGCATGCATCTC
AATTAGTCAGCAACCAGGTGTGGAAAGTCCCCAGGCTCCCCAGCAGGCAGAAGTATGCAAAGCATGCATCTC
AATTAGTCAGCAACCATAGTCCCGCCCCTAACTCCGCCCATCCCGCCCCTAACTCCGCCCAGGATCCGCTCT
AGATGGCCATTGCATACGTTGTATCCATATCATAATATGTACATTTATATTGGCTCATGTCCAACATTACCG
CCATGTTGACATTGATTATTGACTAGTTATTAATAGTAATCAATTACGGGGTCATTAGTTCATAGCCCATAT
ATGGAGTTCCGCGTTACATAACTTACGGTAAATGGCCCGCCTGGCTGACCGCCCAACGACCCCCGCCCATTG
ACGTCAATAATGACGTATGTTCCCATAGTAACGCCAATAGGGACTTTCCATTGACGTCAATGGGTGGAGTAT
TTACGGTAAACTGCCCACTTGGCAGTACATCAAGTGTATCATATGCCAAGTACGCCCCCTATTGACGTCAAT
GACGGTAAATGGCCCGCCTGGCATTATGCCCAGTACATGACCTTATGGGACTTTCCTACTTGGCAGTACATC
TACGTATTAGTCATCGCTATTACCATGGTGATGCGGTTTTGGCAGTACATCAATGGGCGTGGATAGCGGTTT
GACTCACGGGGATTTCCAAGTCTCCACCCCATTGACGTCAATGGGAGTTTGTTTTGGCACCAAAATCAACGG
GACTTTCCAAAATGTCGTAACAACTCCGCCCCATTGACGCAAATGGGCGGTAGGCGTGTACGGTGGGAGGTC
TATATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGCTCGCATCTCTCCTTCACGCGCCCGCCGCCCTACCTGAGG
CCGCCATCCACGCCGGTTGAGTCGCGTTCTGCCGCCTCCCGCCTGTGGTGCCTCCTGAACTGCGTCCGCCGT
CTAGGTAAGTTTAAAGCTCAGGTCGAGACCGGGCCTTTGTCCGGCGCTCCCTTGGAGCCTACCTAGACTCAG
```

-continued

```
CCGGCTCTCCACGCTTTGCCTGACCCTGCTTGCTCAACTCTAGTTCTCTCGTTAACTTAATGAGACAGATAG

AAACTGGTCTTGTAGAAACAGAGTAGTCGCCTGCTTTTCTGCCAGGTGCTGACTTCTCTCCCCTGGGCTTTT

TTCTTTTTCTCAGGTTGAAAAGAAGAAGACGAAGAAGACGAAGAAGACAAACCGTCGTCGACAAGCTTGGTA

CCGAGCTCGGATCCGCCGCCACCATGGAAACGGACACGCTGCTGTGGGTCCTGCTGCTGTGGGTCCCCG

GATCGACGGGAGACGGATCGATGCACCAAAAGCGAACCGCTATGTTTCAGGACCCCCAGGAACGACCCCGTA

AACTGCCCCAGCTCTGCACGGAACTGCAAACGACGATCCATGACATCATCCTCGAATGCGTGTACTGCAAGC

AACAGCTCCTGCGACGTGAAGTCTACGACTTTGCTTTTCGCGACCTGTGCATCGTCTACAGAGACGGAAACC

CCTACGCTGTGGGAGACAAATGCCTGAAGTTTTACTCGAAAATCTCGGAATACCGCCACTACTGCTACTCGC

TGTACGGAACCACGCTCGAACAGCAATACAACAAACCCCTATGCGACCTGCTAATCCGCTGCATCAACTGCC

AAAAGCCTCTCTGCCCTGAAGAAAAGCAACGCCATCTCGACAAAAAGCAAAGATTTCACAACACGCGTGGAC

GATGGACCGGACGATGCATGTCGTGCTGCAGATCGTCACGCACGCGTAGAGAAACCCAGCTGGCTGGAGCTA

TGCATGGAGATACGCCTACGCTCCATGAATATATGCTCGATCTGCAACCCGAAACGACCGATCTCTACGGAT

ATGGACAACTTAACGACTCGTCGGAAGAAGAAGATGAAATCGATGGACCCGCTGGACAAGCTGAACCCGACC

GTGCTCATTACAACATCGTCACGTTTTGTTGCAAGTGTGACTCGACGCTGCGACTGTGCGTCCAATCGACCC

ACGTGGACATCCGTACGCTCGAAGACCTGCTCATGGGAACGCTTGGAATCGTCTGCCCCATCTGCTCGCAGA

AACCCTAATGACTCGAGAGATCTTTTTCCCTCTGCCAAAAATTATGGGGACATCATGAAGCCCCTTGAGCAT

CTGACTTCTGGCTAATAAAGGAAATTTATTTTCATTGCAATAGTGTGTTGGAATTTTTTGTGTCTCTCACTC

GGAAGGACATAAGGGCGGCC
```

NTC8485-O-Ubi-E6[C70G, I135T]-AGA-E7[C24G, E26G]

(SEQ ID NO: 10)

```
GCTAGCCCGCCTAATGAGCGGGCTTTTTTTTCTTAGGCTGCCTCGCGCGTTTCGGTGATGACGGTGAAAACC

TCTGACACATGCAGCTCCCGGAGACGGTCACAGCTTGTCTGTAAGCGGATGCCGGGAGCAGACAAGCCCGTC

AGGGCGCGTCAGCGGGTGTTGGCGGGTGTCGGGGCGCAGCCATGACCCAGTCACGTAGCGATAGCGGAGTGT

ATACTGGCTTAACTATGCGGCATCAGAGCAGATTGTACTGAGAGTGCACCATATGCGGTGTGAAATACCGCA

CAGATGCGTAAGGAGAAAATACCGCATCAGGCGCTCTTCCGCTTCCTCGCTCACTGACTCGCTGCGCTCGGT

CGTTCGGCTGCGGCGAGCGGTATCAGCTCACTCAAAGGCGGTAATACGGTTATCCACAGAATCAGGGGATAA

CGCAGGAAAGAACATGTGAGCAAAAGGCCAGCAAAAGGCCAGGAACCGTAAAAAGGCCGCGTTGCTGGCGTT

TTTCCATAGGCTCCGCCCCCCTGACGAGCATCACAAAAATCGACGCTCAAGTCAGAGGTGGCGAAACCCGAC

AGGACTATAAAGATACCAGGCGTTTCCCCCTGGAAGCTCCCTCGTGCGCTCTCCTGTTCCGACCCTGCCGCT

TACCGGATACCTGTCCGCCTTTCTCCCTTCGGGAAGCGTGGCGCTTTCTCATAGCTCACGCTGTAGGTATCT

CAGTTCGGTGTAGGTCGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACTGGCAGCAGCCACTGG

TAACAGGATTAGCAGAGCGAGGTATGTAGGCGGTGCTACAGAGTTCTTGAAGTGGTGGCCTAACTACGGCTA

CACTAGAAGAACAGTATTTGGTATCTGCGCTCTGCTGAAGCCAGTTACCTTCGGAAAAAGAGTTGGTAGCTC

TTGATCCGGCAAACAAACCACCGCTGGTAGCGGTGGTTTTTTTGTTTGCAAGCAGCAGATTACGCGCAGAAA

AAAAGGATCTCAAGAAGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTAAAAATGAAGTTTTAA

ATCAATCTAAAGTATATATGAGTAAACTTGGTCTGACAGTTACCAATGCTTAATCAGTGAGGCACCTATCTC

AGCGATCTGTCTATTTCGTTCATCCATAGTTGCCTGACTCCTGCAAACCACGTTGTGGTAGAATTGGTAAAG

AGAGTCGTGTAAAATATCGAGTTCGCACATCTTGTTGTCTGATTATTGATTTTGGCGAAACCATTTGATCA

TATGACAAGATGTGTATCTACCTTAACTTAATGATTTTGATAAAAATCATTAGGTACCCCTGATCACTGTGG

AATGTGTGTCAGTTAGGGTGTGGAAAGTCCCCAGGCTCCCCAGCAGGCAGAAGTATGCAAAGCATGCATCTC
```

```
                          -continued
AATTAGTCAGCAACCAGGTGTGGAAAGTCCCCAGGCTCCCCAGCAGGCAGAAGTATGCAAAGCATGCATCTC

AATTAGTCAGCAACCATAGTCCCGCCCCTAACTCCGCCCATCCCGCCCCTAACTCCGCCCAGGATCCGCTCT

AGATGGCCATTGCATACGTTGTATCCATATCATAATATGTACATTTATATTGGCTCATGTCCAACATTACCG

CCATGTTGACATTGATTATTGACTAGTTATTAATAGTAATCAATTACGGGGTCATTAGTTCATAGCCCATAT

ATGGAGTTCCGCGTTACATAACTTACGGTAAATGGCCCGCCTGGCTGACCGCCCAACGACCCCCGCCCATTG

ACGTCAATAATGACGTATGTTCCCATAGTAACGCCAATAGGGACTTTCCATTGACGTCAATGGGTGGAGTAT

TTACGGTAAACTGCCCACTTGGCAGTACATCAAGTGTATCATATGCCAAGTACGCCCCCTATTGACGTCAAT

GACGGTAAATGGCCCGCCTGGCATTATGCCCAGTACATGACCTTATGGGACTTTCCTACTTGGCAGTACATC

TACGTATTAGTCATCGCTATTACCATGGTGATGCGGTTTTGGCAGTACATCAATGGGCGTGGATAGCGGTTT

GACTCACGGGGATTTCCAAGTCTCCACCCCATTGACGTCAATGGGAGTTTGTTTTGGCACCAAAATCAACGG

GACTTTCCAAAATGTCGTAACAACTCCGCCCCATTGACGCAAATGGGCGGTAGGCGTGTACGGTGGGAGGTC

TATATAAGCAGAGCTCGTTTAGTGAACCGTCAGATCGCCTGGAGACGCCATCCACGCTGTTTTGACCTCCAT

AGAAGACACCGGGACCGATCCAGCCTCCGCGGCTCGCATCTCTCCTTCACGCGCCCGCCGCCCTACCTGAGG

CCGCCATCCACGCCGGTTGAGTCGCGTTCTGCCGCCTCCCGCCTGTGGTGCCTCCTGAACTGCGTCCGCCGT

CTAGGTAAGTTTAAAGCTCAGGTCGAGACCGGGCCTTTGTCCGGCGCTCCCTTGGAGCCTACCTAGACTCAG

CCGGCTCTCCACGCTTTGCCTGACCCTGCTTGCTCAACTCTAGTTCTCTCGTTAACTTAATGAGACAGATAG

AAACTGGTCTTGTAGAAACAGAGTAGTCGCCTGCTTTTCTGCCAGGTGCTGACTTCTCTCCCCTGGGCTTTT

TTCTTTTTCTCAGGTTGAAAAGAAGAAGACGAAGAAGACGAAGAAGACAAACCGTCGTCGACAAGCTTGGTA

CCGAGCTCGGATCCGCCGCCACCATGCAAATCTTTGTGAAGACGCTGACGGGAAAGACCATCACGCTCGAAG

TGGAACCCTCGGACACGATCGAAAACGTGAAAGCTAAGATCCAGGACAAGGAAGGAATCCCCCCCGACCAGC

AGAGACTGATCTTTGCTGGAAAGCAGCTCGAAGACGGACGCACGCTGTCGGACTACAACATCCAGAAAGAAT

CGACGCTCCACCTGGTCCTGAGACTCCGCGGAGCTATGCACCAAAAGCGAACCGCTATGTTTCAGGACCCCC

AGGAACGACCCCGTAAACTGCCCCAGCTCTGCACGGAACTGCAAACGACGATCCATGACATCATCCTCGAAT

GCGTGTACTGCAAGCAACAGCTCCTGCGACGTGAAGTCTACGACTTTGCTTTTCGCGACCTGTGCATCGTCT

ACAGAGACGGAAACCCCTACGCTGTGGGAGACAAATGCCTGAAGTTTTACTCGAAAATCTCGGAATACCGCC

ACTACTGCTACTCGCTGTACGGAACCACGCTCGAACAGCAATACAACAAACCCTATGCGACCTGCTAATCC

GCTGCATCAACTGCCAAAAGCCTCTCTGCCCTGAAGAAAAGCAACGCCATCTCGACAAAAAGCAAAGATTTC

ACAACACGCGTGGACGATGGACCGGACGATGCATGTCGTGCTGCAGATCGTCACGCACGCGTAGAGAAACCC

AGCTGGCTGGAGCTATGCATGGAGATACGCCTACGCTCCATGAATATATGCTCGATCTGCAACCCGAAACGA

CCGATCTCTACGGATATGGACAACTTAACGACTCGTCGGAAGAAGAAGATGAAATCGATGGACCCGCTGGAC

AAGCTGAACCCGACCGTGCTCATTACAACATCGTCACGTTTTGTTGCAAGTGTGACTCGACGCTGCGACTGT

GCGTCCAATCGACCCACGTGGACATCCGTACGCTCGAAGACCTGCTCATGGGAACGCTTGGAATCGTCTGCC

CCATCTGCTCGCAGAAACCCTAATGACTCGAGAGATCTTTTTCCCTCTGCCAAAAATTATGGGGACATCATG

AAGCCCCTTGAGCATCTGACTTCTGGCTAATAAAGGAAATTTATTTTCATTGCAATAGTGTGTTGGAATTTT

TTGTGTCTCTCACTCGGAAGGACATAAGGGCGGCC
```

Mice Studies

C57BL/6 mice were provided by the Animal Research Centre in Perth, Australia. All mice were kept under specific pathogen-free conditions at the Biological Research Facility of the Translational Research Institute (Brisbane, Australia), were female and were used at 6-10 weeks of age. All animal procedures and experiments were performed in compliance with the ethical guidelines of the National Health and Medical Research Council of Australia, with approval from the IMVS Animal Ethics Committee and the University of Queensland Animal Ethics Committee (# DI/506/09/UQ).

Immunizations

Mice were immunized twice at a 3 week interval, intradermally in the pinna of each ear with 10 µg HPV DNA vaccine (NTC8485-O-U-E6[C70G, I135T]-AGA-E7[C24G, E26G] and NTC8485-O-s-E6[C70G, I135T]-AGA-E7 [C24G, E26G]) (i.e. 5 ug per ear) or with 30 µg of pcDNA3-E6 or pcDNA3-E7 (i.e., 15 µg/ear). Five mice were used per group and the experiment was carried out in duplicate.

ELISPOT

HPV16 E6 and E7-specific CD8+ T cell responses were measured using IFNγ ELISPOT. Spleens were collected at the conclusion of the experiment, 1 week after the second immunisation, and were pooled for analysis. Preparation of the spleen cells and the ELISPOT protocol were similar to the method used for a HSV glycoprotein D IFN-γ ELISPOT which has been previously described (Dutton et al., 2013). Briefly, $2 \times 10^6$ cells were plated in triplicate in DMEM medium containing 10% FCS in 96 well ELISPOT plates (Millipore) coated with 8 µg capture monoclonal antibody against IFN-γ (AN18, Mabtech AB, Stockholm, Sweden). Cells were restimulated with 20 µg/ml HPV16-E6/E7 peptides (Auspep/Mimotopes) for 24 hours at 37° C. After washing, the plates were incubated for 2 hours at room temperature with a biotinylated monoclonal antibody against IFN-γ (R4-6A2, Mabtech AB, Stockholm, Sweden). For detection, horseradish peroxidase-conjugated strepavidin (Sigma-Aldrich, St Louis, Mo.) and DAB tablets (Sigma-Aldrich, St Louis, Mo.) were used. Spots were counted using an automated ELISPOT reader system ELRO2 (Autoimmun Diagnostika GmbH, Strassberg, Germany).

ELISA

To determine antibody responses to E7, serum was collected from animals on day −1 and on the final day of the experiment (day 28). Maxisorp microtiter plates (Nunc, Roskilde, Denmark) were coated overnight at 4° C. with 50 µl of 0.25 µg/ml HPV16 E7 recombinant protein (Bioclone) in binding buffer (0.7 g $Na_2CO_3$±1.46 g $NaHCO_3$ in 500 mL). After coating, plates were washed three times with PBS/0.1% Tween (PBS-T) and blocked for two hours at 37° C. with 100 µl of 5% skim milk powder in PBS-T. Plates were washed with PBS-T and 50 µl of mouse sera at a dilution of 1:100 were added in duplicate and the plates incubated for one hour at 37° C. After washing three times, 50 µl of anti-mouse IgG peroxidase conjugate (Sigma) were added to each well and the plates incubated for one hour at 37° C. Plates were then washed again three times and incubated with OPD (o-phenylenediamine dihydrochloride) substrate (Sigma, St. Louis, Mo.). Absorbance was measured after 30 min and the addition of 25 µl of 3N HCl, at 492 nm in a Multiskan EX plate reader (Pathtech; Melbourne, Australia).

Statistical Analysis

Statistical analysis was performed with GraphPad Prism version 5.03 for Windows (GraphPad Software, San Diego, Calif.). HPV16-E7 peptide-specific T cell responses were compared by unpaired two-tailed t-test. Antibody titres were compared by One-way ANOVA followed by Tukey's Multiple Comparison test. Differences were considered significant if $P<0.05$.

Example 2

Efficacy of HPV E6E7 Polynucleotide Construct System as Compared to Immunization with E6E7 Fusion Protein Immunogenicity Analysis In order to show that the HPV E6E7-encoding polynucleotide constructs as described above are efficacious as compared to a corresponding E6E7 polypeptide vaccine, mice were divided into groups and exposed to one of the following treatment regimens (with eight mice in each group):
  A. 2×30 µg HPV E6E7-encoding polynucleotide construct system administered intradermally (ID);
  B. 2×30 µg HPV E6E7 fusion protein administered subcutaneously (SC);
  C. 2×30 µg Unimmunized (i.e., irrelevant vector administered ID (negative control).

The experiment occurred over the following timeframe:

| Day (from first immunization) | Action |
| --- | --- |
| −1 | Prebleed |
| 0 | 1st immunization |
| 21 | 2nd immunization |
| 28 | Skin grafts |
| 35 | Graft assessment |
| 37-78 | Graft monitoring |
| 79 | Final bleeds and harvesting of grafts |

Figure 4:
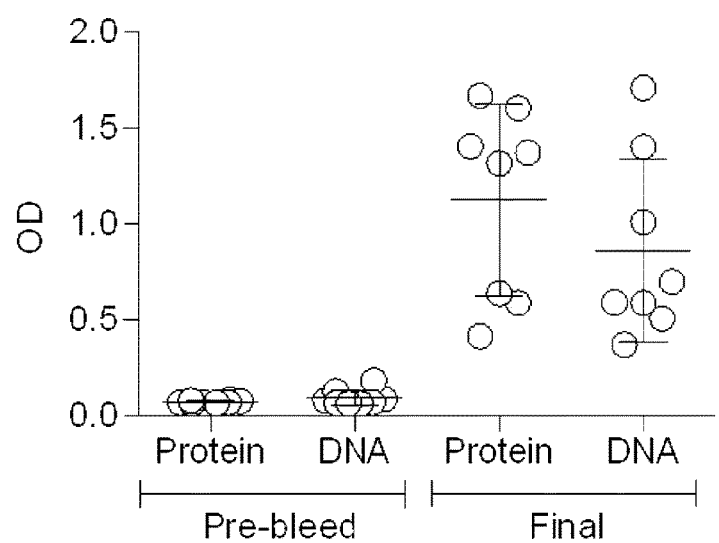
FIG. 4 is a graphical representation of the immunogenicity of the E6E7 polynucleotide construct system compared to an E6E7 fusion protein. (A) HPV16 E7-specific IgG antibody titre in serum at 0 weeks (pre-bleed) and 5 weeks (final). Each data point represents means of duplicates of one individual animal. Mean values and standard deviations are indicated. Optical density (OD). (B) HPV-specific T cell response measured by IFN-γ ELISPOT upon restimulation of splenocytes with HPV16 E6 and E7 peptides. Each data point represents one individual animal. Indicated are means and standard deviations (SD).
Figure 4:
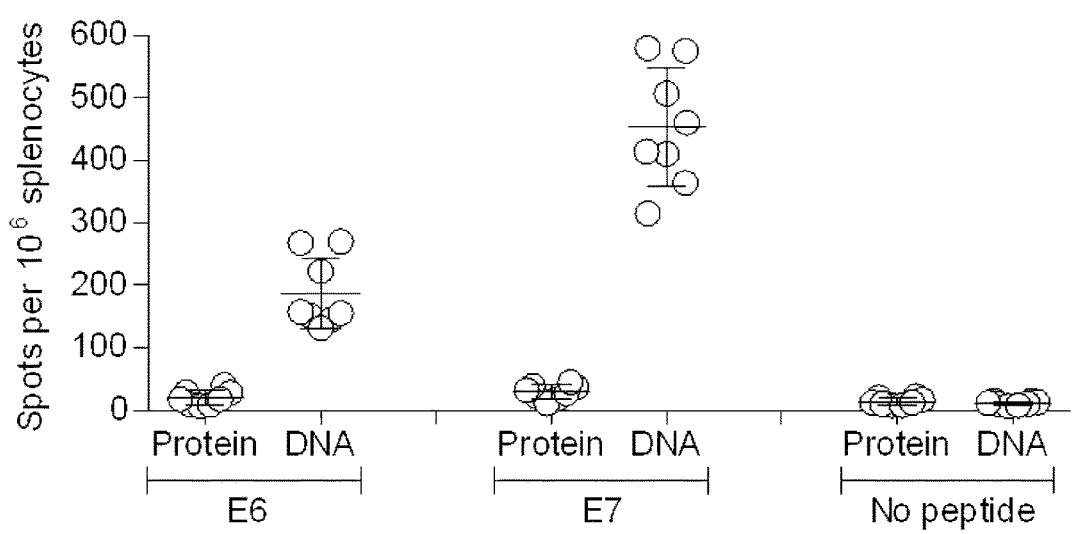

Splenocytes were analysed for E6- and E7-specific T cell responses by IFN-γ ELISPOT at the end of the study. We observed a comparable E7-specific antibody response upon vaccination with E6E7 fusion protein or HPV DNA vaccine (FIG. 4A). However, only the HPV DNA vaccine but not E6E7 fusion protein induced E6- and E7-specific cell-mediated immunity (FIG. 4B).

Skin Graft Model

While many vaccines have been efficacious in accepted animal models, they have subsequently been insufficiently efficacious in clinical trials. As a result, an established skin graft model was used, employing the E7 TCR-β chain transgenic mouse (Narayan et al., 2009). With this model each transgenic animal receives two skin grafts one from donor mice C57/6J.K14E7 (expressing the E7 protein) and the other from donor mice C57BL/6J (control). These transgenic mice produce naive E7-specific TCR transgenic T cells, which assist the vaccine-induced immune response to shrink the graft expressing the E7 protein.

In the skin graft model, the skin of mice expressing HPV-16 E7 as a transgene from the keratin 14 (K14) promoter in keratinocytes, but not in professional antigen-presenting cells, is grafted onto the transgenic mice. It has previously been demonstrated that K14E7 skin grafts are not rejected spontaneously, despite the generation of E7-specific humoral immunity in graft recipients (Dunn et al., Virology, 1997, 253(1): 94-103).

Figure 5:
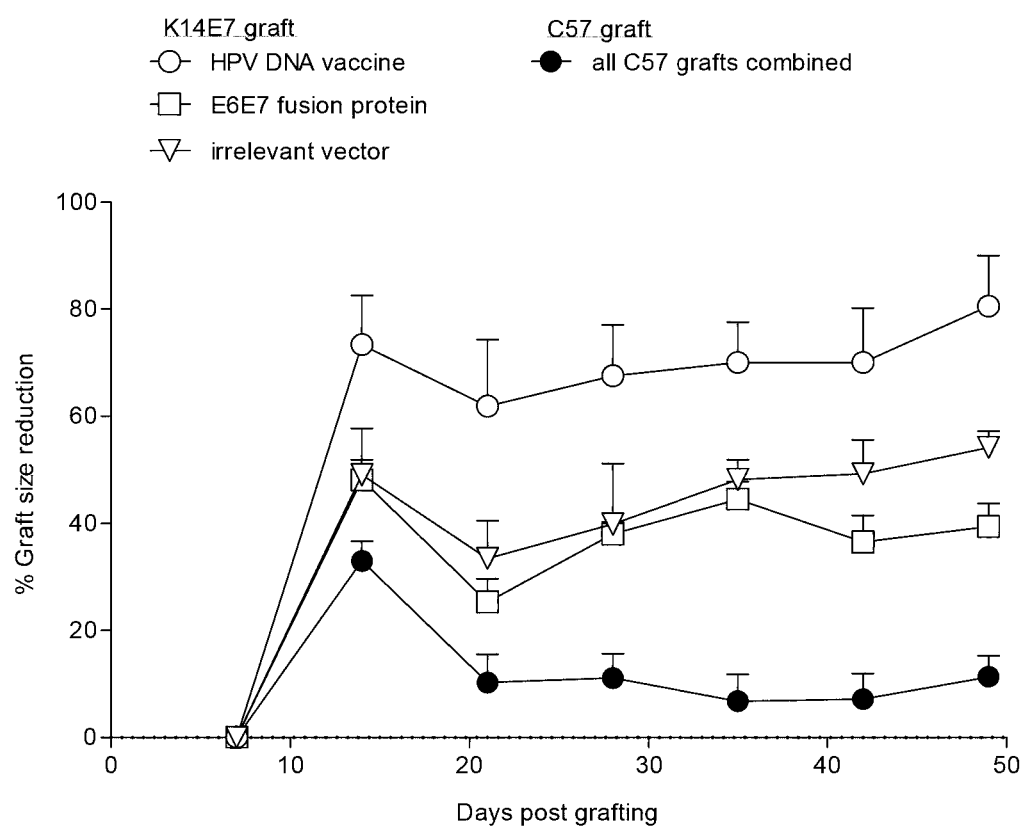
FIG. 5 shows a plot of the percentage reduction in K14E7 graft and C57 control graft size from day 7 to day 49 post grafting in mice immunised with E6E7 polynucleotide construct system (HPV DNA vaccine), E6E7 fusion protein or an irrelevant DNA vaccine. Graft sizes were calculated from photographs using Fiji imaging software. Graft size at day 7 was defined as baseline and the percentage of graft size reduction was calculated relative to this. The graph shows mean values of the percentage of graft size shrinkage from each experimental group with standard error of means (SEM) indicated. White symbols represent K14E7 grafts and black symbols represent control grafts (C57).

Accordingly, groups of six 6 to 8 week-old E7TCR269 mice were immunised twice, three weeks apart by delivery of 30 µg HPV DNA vaccine or irrelevant vector intradermally (ID) to the ear pinnae, or with 30 µg E6E7 fusion protein to the tail base. Mice subsequently received C57BL/6 (control) and K14E7 (HPV16 E7-expressing) skin grafts one week after the second immunization. Grafts were monitored every three days and photos including a ruler taken weekly to calculate graft sizes. We observed that HPV DNA vaccination, but not E6E7 fusion protein vaccination, induced K14E7 graft shrinkage that was significantly different from shrinkage induced by vaccination with irrelevant vector (FIG. 5).

The data presented herein clearly demonstrate that immunization with E6E7 fusion protein alone does not induce an HPV-specific T cell response or rejection of E7-expressing skin grafts. In contrast, immunization with the HPV DNA vaccine induced robust E6- and E7-specific activation of T cells measured by IFN-γ release, and a significant reduction in the size of E7-expressing skin grafts.

Materials and Methods

Mice Studies

C57BL/6J and C57/6J.K14E7 mice were provided by the Animal Research Centre in Perth, Australia. E7TCR269 mice were obtained from Graham Leggatt (Narayan et al., 2009) and were bred in-house (Biological Research Facility of the Translational Research Institute, Brisbane). All mice were kept under specific pathogen-free conditions at the Biological Research Facility of the Translational Research Institute (Brisbane, Australia), were female and were used at 6-12 weeks of age. All animal procedures and experiments were performed in compliance with the ethical guidelines of the National Health and Medical Research Council of Australia, with approval from the IMVS Animal Ethics Committee and the University of Queensland Animal Ethics Committee (#093/15 and #351/15).

Immunizations

For DNA vaccine immunizations, C57BL/6 or E7TCR269 mice were immunized twice 3 weeks apart intradermally in the pinna of each ear with 30 µg HPV DNA vaccine (NTC8485-O-U-E6[C70G, I135T]-AGA-E7[C24G, E26G] and NTC-O-s-E6[C70G, I135T]-AGA-E7[C24G, E26G]). For the E6/E7 fusion protein immunizations C57BL/6 or E7TCR269 mice were immunized twice 3 weeks apart subcutaneously into the tail base with 30 µg of protein, based on a previous publication (Stewart et al., 2004).

Skin Transplantation

E7TCR269 mice received double skin grafts from C57BL/6J donor mice (head end) and C57/6J.K14E7 donor mice (tail end) 7 days after the second immunization. Skin transplantation has been described previously (Mittal et al. 2013). Briefly, donor ear skin was split into dorsal and ventral surfaces (~1 $cm^2$) and the dorsal ear surfaces were placed onto the thoracic flank region of anesthetized E7TCR269 recipients. Grafts were covered with antibiotic-permeated gauze (Bactigras, Smith and Nephew, London, UK) and bandaged with Micropore tape and Flex-wrap (Lyppard, Queensland, Australia). Bandages were removed 7 days later and grafts were monitored for 6 weeks. Photographs including a ruler were taken weekly and graft size was analysed using Fiji Imagine software.

ELISPOT

HPV16 E6 and E7-specific CD8+ T cell responses were measured using IFN-γ ELISPOT. The ELISPOT protocol has been previously described (Dutton et al., 2013). Briefly, $1\times10^6$ cells were plated in triplicate in DMEM medium containing 10% FCS in 96 well ELISPOT plates (Millipore) coated with 8 µg capture monoclonal antibody against IFN-γ (AN18, Mabtech AB, Stockholm, Sweden). Cells were restimulated with 10 µg/ml HPV16-E6/E7 peptides (Auspep/Mimotopes) for 24 hours at 37° C. After washing, plates were incubated for 2 hours at room temperature with a biotinylated monoclonal antibody against IFN-γ (R4-6A2, Mabtech AB, Stockholm, Sweden). For detection, horseradish peroxidase-conjugated strepavidin (Sigma-Aldrich, St Louis, Mo.) and DAB tablets (Sigma-Aldrich, St Louis, Mo.) were used. Spots were counted using an automated ELISPOT reader system ELRO2 (Autoimmun Diagnostika GmbH, Strassberg, Germany).

ELISA

To determine antibody responses, serum was collected from animals on day −1 and on the final day of the experiment (day 77). Maxisorp microtiter plates (Nunc, Roskilde, Denmark) were coated overnight at 4° C. with 50 µl of 0.25 µg/ml with HPV16-E7 recombinant protein (Bioclone). After coating, plates were washed three times with PBS/0.1% Tween (PBS-T) and blocked for two hours at 37° C. with 100 µl of 5% skim milk powder in PBS-T. Plates were washed with PBS-T, in duplicate 50 µl of mouse sera (at a dilution of 1:100) were added per well, and the plates then incubated for one hour at 37° C. After washing three times, 50 µl of anti-mouse IgG peroxidase conjugate (Sigma) was incubated for one hour at 37° C. Plates were washed again three times and incubated with OPD (o-phenylenediamine dihydrochloride) substrate (Sigma, St. Louis, Mo.). Absorbance was measured after 30 min and the addition of 25 µl of 3N HCl, at 492 nm in a Multiskan EX plate reader (Pathtech; Melbourne, Australia).

Statistical Analysis

Statistical analysis was performed with GraphPad Prism version 5.03 for Windows (GraphPad Software, San Diego, Calif.). Skin transplant survival curves were compared by the Mantel-Cox test. HPV16-E7 peptide-specific T cell responses were compared by unpaired two-tailed t-tests. Antibody titers were compared by One-way ANOVA followed by Tukey's Multiple Comparison test. Differences were considered significant if $P<0.05$.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

---

What is claimed is:

1. A construct system for the treatment of human papillomavirus (HPV) infection in a subject, wherein the system comprises a first nucleic acid construct and a second nucleic acid construct, wherein the first construct comprises a first synthetic coding sequence that encodes a first polypeptide sequence comprising an HPV E6 amino acid sequence conjugated to a HPV E7 amino acid sequence, and wherein the first synthetic coding sequence comprises the polynucleotide sequence set forth in SEQ ID NO: 7 and is operably connected to a regulatory nucleic acid sequence; and wherein the second construct comprises a second synthetic coding sequence that encodes a first polypeptide sequence comprising an HPV E6 amino acid sequence conjugated to a HPV E7 amino acid sequence, wherein the HPV E6 and E7 amino acid sequences are encoded by a HPV E6 and E7 coding sequence, respectively, that are both distinguished from a wild-type HPV E6 and E7 coding sequence, respectively, by the replacement of selected codons in the wild-type HPV E6 or E7 coding sequence with synonymous codons, wherein an individual synonymous codon has a preference for producing a greater immune response than a corresponding selected codon, wherein the codon replacements are selected from TABLE 1, and wherein at least about 70%, 75%, 80%, 85%, 90%, 91%, 92%, 93%, 94%, 95%, 96%, 97%, 98%, 99%, or 100%, of the codons for the first synthetic coding sequence are synonymous codons according to TABLE 1, and wherein the first synthetic coding sequence is operably connected to a regulatory nucleic acid sequence; and to a nucleic acid sequence that encodes a ubiquitin molecule; and wherein TABLE 1 is as follows:

TABLE 1

| Wild-type Codon | Synonymous Codon |
|---|---|
| Ala$^{GCG}$ | Ala$^{GCT}$ |
| Ala$^{GCG}$ | Ala$^{GCC}$ |
| Ala$^{GCA}$ | Ala$^{GCT}$ |
| Ala$^{GCA}$ | Ala$^{GCC}$ |
| Ala$^{GCC}$ | Ala$^{GCT}$ |
| Arg$^{CGG}$ | Arg$^{CGA}$ |
| Arg$^{CGG}$ | Arg$^{CGC}$ |
| Arg$^{CGG}$ | Arg$^{CGT}$ |
| Arg$^{CGG}$ | Arg$^{AGA}$ |
| Arg$^{AGG}$ | Arg$^{CGA}$ |
| Arg$^{AGG}$ | Arg$^{CGC}$ |
| Arg$^{AGG}$ | Arg$^{CGT}$ |
| Arg$^{AGG}$ | Arg$^{AGA}$ |
| Asn$^{AAT}$ | Asn$^{AAC}$ |
| Asp$^{GAT}$ | Asp$^{GAC}$ |
| Cys$^{TGT}$ | Cys$^{TGC}$ |
| Glu$^{GAG}$ | Glu$^{GAA}$ |
| Gly$^{GGC}$ | Gly$^{GGA}$ |
| Gly$^{GGT}$ | Gly$^{GGA}$ |
| Gly$^{GGG}$ | Gly$^{GGA}$ |
| Ile$^{ATA}$ | Ile$^{ATC}$ |
| Ile$^{ATA}$ | Ile$^{ATT}$ |
| Ile$^{ATT}$ | Ile$^{ATC}$ |
| Leu$^{TTA}$ | Leu$^{CTG}$ |
| Leu$^{TTA}$ | Leu$^{CTC}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTG}$ |
| Leu$^{TTG}$ | Leu$^{CTC}$ |
| Leu$^{TTG}$ | Leu$^{CTA}$ |
| Leu$^{TTG}$ | Leu$^{CTT}$ |
| Leu$^{CTT}$ | Leu$^{CTG}$ |
| Leu$^{CTT}$ | Leu$^{CTC}$ |
| Leu$^{CTA}$ | Leu$^{CTG}$ |
| Leu$^{CTA}$ | Leu$^{CTC}$ |
| Phe$^{TTC}$ | Phe$^{TTT}$ |
| Pro$^{CCG}$ | Pro$^{CCC}$ |
| Pro$^{CCG}$ | Pro$^{CCT}$ |
| Pro$^{CCA}$ | Pro$^{CCC}$ |
| Pro$^{CCA}$ | Pro$^{CCT}$ |
| Pro$^{CCT}$ | Pro$^{CCC}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGT}$ | Ser$^{TCC}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACC}$ |
| Thr$^{ACT}$ | Thr$^{ACA}$ |
| Thr$^{ACA}$ | Thr$^{ACG}$ |
| Thr$^{ACA}$ | Thr$^{ACC}$ |
| Thr$^{ACC}$ | Thr$^{ACG}$ |
| Tyr$^{TAT}$ | Tyr$^{TAC}$ |
| Val$^{GTA}$ | Val$^{GTG}$ |
| Val$^{GTA}$ | Val$^{GTC}$ |
| Val$^{GTA}$ | Val$^{GTT}$ |
| Val$^{GTT}$ | Val$^{GTG}$ |
| Val$^{GTT}$ | Val$^{GTC}$. |

2. A method of treating a human papillomavirus (HPV) infection in a subject, the method comprising administering concurrently to the subject an effective amount of the construct system according to claim 1.

3. The system according to claim 1, wherein the nucleic acid that encodes the ubiquitin molecule comprises at least a portion of the sequence set forth in SEQ ID NO: 5.

4. A construct system for the treatment of human Papillomavirus (HPV) infection in a subject, wherein the system comprises a first nucleic acid construct and a second nucleic acid construct, wherein the first construct comprises a first synthetic coding sequence that encodes a first polypeptide sequence comprising an HPV E6 amino acid sequence conjugated to a HPV E7 amino acid sequence, wherein the HPV E6 and E7 amino acid sequences are encoded by a HPV E6 and E7 coding sequence, respectively, that are both distinguished from a wild-type HPV E6 and E7 coding sequence, respectively, by the replacement of selected codons in the wild-type HPV E6 or E7 coding sequence with synonymous codons, wherein an individual synonymous codon has a preference for producing a greater immune response than a corresponding selected codon, wherein the codon replacements are selected from TABLE 1, wherein at least about 70%, 75%, 80%, 85%, 90%, 91%, 92%, 93%, 94%, 95%, 96%, 97%, 98%, 99%, or 100%, of the codons for the first synthetic coding sequence are synonymous codons according to TABLE 1, and wherein the first synthetic coding sequence is operably connected to a regulatory nucleic acid sequence; and wherein the second construct comprises a second synthetic coding sequence that encodes a first polypeptide sequence comprising an HPV E6 amino acid sequence conjugated to a HPV E7 amino acid sequence, and wherein the second synthetic coding sequence comprises the polynucleotide sequence set forth in SEQ ID NO: 8 and is operably connected to a regulatory nucleic acid sequence and to a nucleic acid sequence that encodes a ubiquitin molecule; and wherein TABLE 1 is as follows:

TABLE 1

| Wild-type Codon | Synonymous Codon |
|---|---|
| Ala$^{GCG}$ | Ala$^{GCT}$ |
| Ala$^{GCG}$ | Ala$^{GCC}$ |
| Ala$^{GCA}$ | Ala$^{GCT}$ |
| Ala$^{GCA}$ | Ala$^{GCC}$ |
| Ala$^{GCC}$ | Ala$^{GCT}$ |
| Arg$^{CGG}$ | Arg$^{CGA}$ |
| Arg$^{CGG}$ | Arg$^{CGC}$ |
| Arg$^{CGG}$ | Arg$^{CGT}$ |
| Arg$^{CGG}$ | Arg$^{AGA}$ |
| Arg$^{AGG}$ | Arg$^{CGA}$ |
| Arg$^{AGG}$ | Arg$^{CGC}$ |
| Arg$^{AGG}$ | Arg$^{CGT}$ |
| Arg$^{AGG}$ | Arg$^{AGA}$ |
| Asn$^{AAT}$ | Asn$^{AAC}$ |
| Asp$^{GAT}$ | Asp$^{GAC}$ |
| Cys$^{TGT}$ | Cys$^{TGC}$ |
| Glu$^{GAG}$ | Glu$^{GAA}$ |
| Gly$^{GGC}$ | Gly$^{GGA}$ |
| Gly$^{GGT}$ | Gly$^{GGA}$ |
| Gly$^{GGG}$ | Gly$^{GGA}$ |
| Ile$^{ATA}$ | Ile$^{ATC}$ |
| Ile$^{ATA}$ | Ile$^{ATT}$ |
| Ile$^{ATT}$ | Ile$^{ATC}$ |
| Leu$^{TTA}$ | Leu$^{CTG}$ |
| Leu$^{TTA}$ | Leu$^{CTC}$ |
| Leu$^{TTA}$ | Leu$^{CTA}$ |
| Leu$^{TTA}$ | Leu$^{CTT}$ |
| Leu$^{TTA}$ | Leu$^{TTG}$ |
| Leu$^{TTG}$ | Leu$^{CTG}$ |
| Leu$^{TTG}$ | Leu$^{CTC}$ |
| Leu$^{TTG}$ | Leu$^{CTA}$ |
| Leu$^{TTG}$ | Leu$^{CTT}$ |
| Leu$^{CTT}$ | Leu$^{CTG}$ |

TABLE 1-continued

| Wild-type Codon | Synonymous Codon |
|---|---|
| Leu$^{CTT}$ | Leu$^{CTC}$ |
| Leu$^{CTA}$ | Leu$^{CTG}$ |
| Leu$^{CTA}$ | Leu$^{CTC}$ |
| Phe$^{TTC}$ | Phe$^{TTT}$ |
| Pro$^{CCG}$ | Pro$^{CCC}$ |
| Pro$^{CCG}$ | Pro$^{CCT}$ |
| Pro$^{CCA}$ | Pro$^{CCC}$ |
| Pro$^{CCA}$ | Pro$^{CCT}$ |
| Pro$^{CCT}$ | Pro$^{CCC}$ |
| Ser$^{AGT}$ | Ser$^{TCG}$ |
| Ser$^{AGT}$ | Ser$^{TCT}$ |
| Ser$^{AGT}$ | Ser$^{TCA}$ |
| Ser$^{AGT}$ | Ser$^{TCC}$ |
| Ser$^{AGC}$ | Ser$^{TCG}$ |
| Ser$^{AGC}$ | Ser$^{TCT}$ |
| Ser$^{AGC}$ | Ser$^{TCA}$ |
| Ser$^{AGC}$ | Ser$^{TCC}$ |
| Ser$^{TCC}$ | Ser$^{TCG}$ |
| Ser$^{TCA}$ | Ser$^{TCG}$ |
| Ser$^{TCT}$ | Ser$^{TCG}$ |
| Thr$^{ACT}$ | Thr$^{ACG}$ |
| Thr$^{ACT}$ | Thr$^{ACC}$ |
| Thr$^{ACT}$ | Thr$^{ACA}$ |
| Thr$^{ACA}$ | Thr$^{ACG}$ |
| Thr$^{ACA}$ | Thr$^{ACC}$ |
| Thr$^{ACC}$ | Thr$^{ACG}$ |
| Tyr$^{TAT}$ | Tyr$^{TAC}$ |
| Val$^{GTA}$ | Val$^{GTG}$ |
| Val$^{GTA}$ | Val$^{GTC}$ |
| Val$^{GTA}$ | Val$^{GTT}$ |
| Val$^{GTT}$ | Val$^{GTG}$ |
| Val$^{GTT}$ | Val$^{GTC}$. |

5. The system according to claim 1, wherein the first synthetic coding sequence comprises the polynucleotide sequence set forth in SEQ ID NO: 7 and the second synthetic coding sequence comprises the polynucleotide sequence set forth in SEQ ID NO: 8.

6. The system according to claim 1, wherein the first construct and the second construct are contained in one or more expression vectors.

7. The system according to claim 1, wherein at least about 75% of the codons in the second synthetic coding sequence are synonymous codons selected from TABLE 1.

8. The system according to claim 1, wherein at least about 85% of the codons in the second synthetic coding sequence are synonymous codons selected from TABLE 1.

9. The system according to claim 1, wherein at least about 95% of the codons in the second synthetic coding sequence are synonymous codons selected from TABLE 1.

10. The system according to claim 1, wherein at least about 98% of the codons in the synthetic coding sequence are synonymous codons selected from TABLE 1.

11. The method according to claim 2, wherein the construct system is administered with an adjuvant.

12. The method according to claim 2, wherein the construct system is administered without an adjuvant.

13. The method according to claim 2, wherein the subject is a human.

14. A pharmaceutical composition comprising the construct system of claim 1, together with a pharmaceutically acceptable carrier, excipient and/or diluent.

15. The system according to claim 4, wherein the first construct and the second construct are contained in one or more expression vectors.

16. The system according to claim 4, wherein at least about 75%, 85%, 90% or 95% of the codons in the first synthetic coding sequence are synonymous codons selected from TABLE 1.

17. A method of treating a human papillomavirus (HPV) infection in a subject, the method comprising administering concurrently to the subject an effective amount of the construct system according to claim 4.

18. The method of claim 17, wherein the construct system is administered with an adjuvant.

19. The method according to claim 17, wherein the subject is a human.

* * * * *

SEQUENCE LISTING

```
<160> NUMBER OF SEQ ID NOS: 10

<210> SEQ ID NO 1
<211> LENGTH: 477
<212> TYPE: DNA
<213> ORGANISM: Human papillomavirus type 16

<400> SEQUENCE: 1
atgcaccaaa agagaactgc aatgtttcag gacccacagg agcgacccag aaagttacca       60
cagttatgca cagagctgca aacaactata catgatataa tattagaatg tgtgtactgc      120
```

```
aagcaacagt tactgcgacg tgaggtatat gactttgctt ttcgggattt atgcatagta      180
tatagagatg ggaatccata tgctgtatgt gataaatgtt taaagttta ttctaaaatt       240 agtgagtata gacattattg ttatagtttg tatggaacaa cattagaaca gcaatacaac      300
aaaccgttgt gtgatttgtt aattaggtgt attaactgtc aaaagccact gtgtcctgaa      360
gaaaagcaaa gacatctgga caaaaagcaa agattccata atataagggg tcggtggacc      420
ggtcgatgta tgtcttgttg cagatcatca agaacacgta gagaaaccca gctgtaa        477
```

<210> SEQ ID NO 2
<211> LENGTH: 158
<212> TYPE: PRT
<213> ORGANISM: Human papillomavirus type 16

<400> SEQUENCE: 2

```
Met His Gln Lys Arg Thr Ala Met Phe Gln Asp Pro Gln Glu Arg Pro
1               5                  10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

<210> SEQ ID NO 3
<211> LENGTH: 297
<212> TYPE: DNA
<213> ORGANISM: Human papillomavirus type 16

<400> SEQUENCE: 3

```
atgcatggag atacacctac attgcatgaa tatatgttag atttgcaacc agagacaact      60
gatctctact gttatgagca attaaatgac agctcagagg aggaggatga aatagatggt      120
ccagctggac aagcagaacc ggacagagcc cattacaata ttgtaacctt ttgttgcaag      180
tgtgactcta cgcttcggtt gtgcgtacaa agcacacacg tagacatccg tacgttggaa      240
gacctgttaa tgggcacact aggaattgtg tgccccatct gttctcagaa accataa        297
```

<210> SEQ ID NO 4
<211> LENGTH: 98
<212> TYPE: PRT
<213> ORGANISM: Human papillomavirus type 16

-continued

<400> SEQUENCE: 4

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 5
<211> LENGTH: 690
<212> TYPE: DNA
<213> ORGANISM: Homo sapiens

<400> SEQUENCE: 5
atgcagatct tcgtgaaaac ccttaccggc aagaccatca cccttgaggt ggagcccagt     60
gacaccatcg aaaatgtgaa ggccaagatc caggataagg aaggcattcc ccccgaccag    120
cagaggctca tctttgcagg caagcagctg aagatggccg tactctttc tgactacaac    180
atccagaagg agtcgaccct gcacctggtc ctgcgtctga ggtggtat gcagatcttc    240
gtgaagaccc tgaccggcaa gaccatcacc ctggaagtgg agcccagtga caccatcgaa    300
aatgtgaagg ccaagatcca ggataaagaa ggcatccctc ccgaccagca gaggctcatc    360
tttgcaggca agcagctgga agatggccgc actctttctg actacaacat ccagaaggag    420
tcgaccctgc acctggtcct gcgtctgaga ggtggtatgc agatcttcgt gaagaccctg    480
accggcaaga ccatcactct ggaggtggag cccagtgaca ccatcgaaaa tgtgaaggcc    540
aagatccaag ataaagaagg catcccccc gaccagcaga ggctcatctt tgcaggcaag    600
cagctggaag atggccgcac tctttctgac tacaacatcc agaaagagtc gaccctgcac    660
ctggtcctgc gcctgagggg tggctgttaa                                    690

<210> SEQ ID NO 6
<211> LENGTH: 76
<212> TYPE: PRT
<213> ORGANISM: Homo sapiens

<400> SEQUENCE: 6

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 7
<211> LENGTH: 849
<212> TYPE: DNA
<213> ORGANISM: Artificial Sequence
<220> FEATURE:
<223> OTHER INFORMATION: HPV E6-E7 synthetic coding sequence

<400> SEQUENCE: 7

```
atggaaacgg acacgctgct gctgtgggtc ctgctgctgt gggtcccgg atcgacggga      60
gacggatcga tgcaccaaaa gcgaaccgct atgtttcagg accccagga acgacccgt     120
aaactgcccc agctctgcac ggaactgcaa cgacgatcc atgacatcat cctcgaatgc    180
gtgtactgca gcaacagct cctgcgacgt gaagtctacg actttgcttt tcgcgacctg    240
tgcatcgtct acagagacgg aaaccccctac gctgtgggag acaaatgcct gaagttttac    300
tcgaaaatct cggaataccg ccactactgc tactcgctgt acggaaccac gctcgaacag    360
caatacaaca acccctatg cgacctgcta atccgctgca tcaactgcca aaagcctctc    420
tgccctgaag aaaagcaacg ccatctcgac aaaaagcaaa gatttcacaa cacgcgtgga    480
cgatggaccg gacgatgcat gtcgtgctgc agatcgtcac gcacgcgtag agaaacccag    540
ctggctggag ctatgcatgg agatacgcct acgctccatg aatatatgct cgatctgcaa    600
cccgaaacga ccgatctcta cggatatgga caacttaacg actcgtcgga agaagaagat    660
gaaatcgatg acccgctgg acaagctgaa cccgaccgtg ctcattacaa catcgtcacg    720
ttttgttgca gtgtgactc gacgctgcga ctgtgcgtcc aatcgaccca cgtggacatc    780
cgtacgctcg aagacctgct catgggaacg cttggaatcg tctgccccat ctgctcgcag    840
aaaccctaa                                                           849
```

<210> SEQ ID NO 8
<211> LENGTH: 1008
<212> TYPE: DNA
<213> ORGANISM: Artificial Sequence
<220> FEATURE:
<223> OTHER INFORMATION: Ubiquitinated HPV E6-E7 synthetic coding
       sequence

<400> SEQUENCE: 8

```
atgcaaatct ttgtgaagac gctgacggga agaccatca cgctcgaagt ggaaccctcg      60
gacacgatcg aaaacgtgaa agctaagatc caggacaagg aaggaatccc cccgaccag     120
cagagactga tctttgctgg aaagcagctc gaagacggac gcacgctgtc ggactacaac    180
atccagaaag aatcgacgct ccacctggtc ctgagactcc gcggagctat gcaccaaaag    240
cgaaccgcta tgtttcagga ccccaggaa cgaccccgta aactgcccca gctctgcacg    300
gaactgcaaa cgacgatcca tgacatcatc ctcgaatgcg tgtactgcaa gcaacagctc    360
ctgcgacgtg aagtctacga ctttgctttt cgcgacctgt gcatcgtcta cagagacgga    420
aaccccctacg ctgtgggaga caaatgcctg aagttttact cgaaaatctc ggaataccgc    480
cactactgct actcgctgta cggaaccacg ctcgaacagc aatacaacaa cccctatgc    540
gacctgctaa tccgctgcat caactgccaa aagcctctct gccctgaaga aaagcaacgc    600
catctcgaca aaaagcaaag atttcacaac acgcgtggac gatggaccgg acgatgcatg    660
tcgtgctgca gatcgtcacg cacgcgtaga gaaacccagc tggctggagc tatgcatgga    720
gatacgccta cgctccatga atatatgctc gatctgcaac ccgaaacgac cgatctctac    780
ggatatggac aacttaacga ctcgtcggaa gaagaagatg aaatcgatgg acccgctgga    840
caagctgaac ccgaccgtgc tcattacaac atcgtcacgt tttgttgcaa gtgtgactcg    900
```

| | |
|---|---:|
| acgctgcgac tgtgcgtcca atcgacccac gtggacatcc gtacgctcga agacctgctc | 960 |
| atgggaacgc ttggaatcgt ctgccccatc tgctcgcaga aaccctaa | 1008 |

<210> SEQ ID NO 9
<211> LENGTH: 3908
<212> TYPE: DNA
<213> ORGANISM: Artificial Sequence
<220> FEATURE:
<223> OTHER INFORMATION: NTC8485-O-s-E6[C70G, I135T]-AGA-E7[C24G, E26G]

<400> SEQUENCE: 9

| | |
|---|---:|
| gctagcccgc ctaatgagcg ggcttttttt tcttaggctg cctcgcgcgt ttcggtgatg | 60 |
| acggtgaaaa cctctgacac atgcagctcc cggagacggt cacagcttgt ctgtaagcgg | 120 |
| atgccgggag cagacaagcc cgtcagggcg cgtcagcggg tgttggcggg tgtcggggcg | 180 |
| cagccatgac ccagtcacgt agcgatagcg gagtgtatac tggcttaact atgcggcatc | 240 |
| agagcagatt gtactgagag tgcaccatat gcggtgtgaa ataccgcaca gatgcgtaag | 300 |
| gagaaaatac cgcatcaggc gctcttccgc ttcctcgctc actgactcgc tgcgctcggt | 360 |
| cgttcggctg cggcgagcgg tatcagctca ctcaaaggcg gtaatacggt tatccacaga | 420 |
| atcaggggat aacgcaggaa agaacatgtg agcaaaaggc cagcaaaagg ccaggaaccg | 480 |
| taaaaaggcc gcgttgctgg cgttttccca taggctccgc cccctgacg agcatcacaa | 540 |
| aaatcgacgc tcaagtcaga ggtggcgaaa cccgacagga ctataaagat accaggcgtt | 600 |
| tccccctgga agctccctcg tgcgctctcc tgttccgacc ctgccgctta ccggatacct | 660 |
| gtccgccttt ctcccttcgg gaagcgtggc gctttctcat agctcacgct gtaggtatct | 720 |
| cagttcggtg taggtcgttc gctccaagct gggctgtgtg cacgaacccc ccgttcagcc | 780 |
| cgaccgctgc gccttatccg gtaactatcg tcttgagtcc aacccggtaa gacacgactt | 840 |
| atcgccactg gcagcagcca ctggtaacag gattagcaga gcgaggtatg taggcggtgc | 900 |
| tacagagttc ttgaagtggt ggcctaacta cggctacact agaagaacag tatttggtat | 960 |
| ctgcgctctg ctgaagccag ttaccttcgg aaaaagagtt ggtagctctt gatccggcaa | 1020 |
| acaaaccacc gctggtagcg tggttttttt gtttgcaag cagcagatta cgcgcagaaa | 1080 |
| aaaaggatct caagaagatc ctttgatctt ttctacgggg tctgacgctc agtggaacga | 1140 |
| aaactcacgt taagggattt tggtcatgag attatcaaaa aggatcttca cctagatcct | 1200 |
| tttaaattaa aaatgaagtt ttaaatcaat ctaaagtata tatgagtaaa cttggtctga | 1260 |
| cagttaccaa tgcttaatca gtgaggcacc tatctcagcg atctgtctat ttcgttcatc | 1320 |
| catagttgcc tgactcctgc aaaccacgtt gtggtagaat tggtaaagag agtcgtgtaa | 1380 |
| aatatcgagt tcgcacatct tgttgtctga ttattgattt ttggcgaaac catttgatca | 1440 |
| tatgacaaga tgtgtatcta ccttaactta atgatttga taaaaatcat taggtacccc | 1500 |
| tgatcactgt ggaatgtgtg tcagttaggg tgtggaaagt ccccaggctc cccagcaggc | 1560 |
| agaagtatgc aaagcatgca tctcaattag tcagcaacca ggtgtggaaa gtccccaggc | 1620 |
| tccccagcag gcagaagtat gcaaagcatg catctcaatt agtcagcaac catagtcccg | 1680 |
| cccctaactc cgcccatccc gcccctaact ccgcccagga tccgctctag atggccattg | 1740 |
| catacgttgt atccatatca taatatgtac atttatattg gctcatgtcc aacattaccg | 1800 |
| ccatgttgac attgattatt gactagttat taatagtaat caattacggg gtcattagtt | 1860 |
| catagcccat atatggagtt ccgcgttaca taacttacgg taaatggccc gcctggctga | 1920 |
| ccgcccaacg acccccgccc attgacgtca ataatgacgt atgttcccat agtaacgcca | 1980 |

| | |
|---|---|
| ataggaactt tccattgacg tcaatgggtg gagtatttac ggtaaactgc ccacttggca | 2040 |
| gtacatcaag tgtatcatat gccaagtacg cccctattg acgtcaatga cggtaaatgg | 2100 |
| cccgcctggc attatgccca gtacatgacc ttatgggact ttcctacttg gcagtacatc | 2160 |
| tacgtattag tcatcgctat taccatggtg atgcggtttt ggcagtacat caatgggcgt | 2220 |
| ggatagcggt ttgactcacg ggatttcca agtctccacc ccattgacgt caatgggagt | 2280 |
| ttgttttggc accaaaatca acgggacttt ccaaaatgtc gtaacaactc cgccccattg | 2340 |
| acgcaaatgg gcggtaggcg tgtacggtgg gaggtctata taagcagagc tcgtttagtg | 2400 |
| aaccgtcaga tcgcctggag acgccatcca cgctgttttg acctccatag aagacaccgg | 2460 |
| gaccgatcca gcctccgcgg ctcgcatctc tccttcacgc gcccgccgcc ctacctgagg | 2520 |
| ccgccatcca cgccggttga gtcgcgttct gccgcctccc gcctgtggtg cctcctgaac | 2580 |
| tgcgtccgcc gtctaggtaa gtttaaagct caggtcgaga ccgggccttt gtccggcgct | 2640 |
| cccttggagc ctacctagac tcagccggct ctccacgctt tgcctgaccc tgcttgctca | 2700 |
| actctagttc tctcgttaac ttaatgagac agatagaaac tggtcttgta gaaacagagt | 2760 |
| agtcgcctgc ttttctgcca ggtgctgact tctctcccct gggcttttt ctttttctca | 2820 |
| ggttgaaaag aagaagacga agaagacgaa gaagacaaac cgtcgtcgac aagcttggta | 2880 |
| ccgagctcgg atccgccgcc accatggaaa cggacacgct gctgctgtgg gtcctgctgc | 2940 |
| tgtgggtccc cggatcgacg ggagacggat cgatgcacca aaagcgaacc gctatgtttc | 3000 |
| aggaccccca ggaacgaccc cgtaaactgc cccagctctg cacggaactg caaacgacga | 3060 |
| tccatgacat catcctcgaa tgcgtgtact gcaagcaaca gctcctgcga cgtgaagtct | 3120 |
| acgactttgc ttttcgcgac ctgtgcatcg tctacagaga cggaaacccc tacgctgtgg | 3180 |
| gagacaaatg cctgaagttt tactcgaaaa tctcggaata ccgccactac tgctactcgc | 3240 |
| tgtacggaac cacgctcgaa cagcaataca acaaacccct atgcgacctg ctaatccgct | 3300 |
| gcatcaactg ccaaaagcct ctctgccctg aagaaaagca acgccatctc gacaaaaagc | 3360 |
| aaagatttca caacacgcgt ggacgatgga ccggacgatg catgtcgtgc tgcagatcgt | 3420 |
| cacgcacgcg tagagaaacc cagctggctg gagctatgca tggagatacg cctacgctcc | 3480 |
| atgaatatat gctcgatctg caacccgaaa cgaccgatct ctacggatat ggacaactta | 3540 |
| acgactcgtc ggaagaagaa gatgaaatcg atggaccgc tggacaagct gaacccgacc | 3600 |
| gtgctcatta acatcgtc acgttttgtt gcaagtgtga ctcgacgctg cgactgtgcg | 3660 |
| tccaatcgac ccacgtggac atccgtacgc tcgaagacct gctcatggga acgcttggaa | 3720 |
| tcgtctgccc catctgctcg cagaaaccct aatgactcga gagatctttt tccctctgcc | 3780 |
| aaaaattatg gggacatcat gaagccccctt gagcatctga cttctggcta ataaggaaa | 3840 |
| tttatttca ttgcaatagt gtgttggaat ttttgtgtc tctcactcgg aaggacataa | 3900 |
| gggcggcc | 3908 |

<210> SEQ ID NO 10
<211> LENGTH: 4067
<212> TYPE: DNA
<213> ORGANISM: Artificial Sequence
<220> FEATURE:
<223> OTHER INFORMATION: NTC8485-O-Ubi-E6[C70G, I135T]-AGA-E7[C24G, E26G]

<400> SEQUENCE: 10

```
gctagcccgc ctaatgagcg ggcttttttt tcttaggctg cctcgcgcgt ttcggtgatg      60
acggtgaaaa cctctgacac atgcagctcc cggagacggt cacagcttgt ctgtaagcgg     120
atgccgggag cagacaagcc cgtcagggcg cgtcagcggg tgttggcggg tgtcggggcg     180
cagccatgac ccagtcacgt agcgatagcg gagtgtatac tggcttaact atgcggcatc     240
agagcagatt gtactgagag tgcaccatat gcggtgtgaa ataccgcaca gatgcgtaag     300
gagaaaatac cgcatcaggc gctcttccgc ttcctcgctc actgactcgc tgcgctcggt     360
cgttcggctg cggcgagcgg tatcagctca ctcaaaggcg gtaatacggt tatccacaga     420
atcaggggat aacgcaggaa agaacatgtg agcaaaaggc cagcaaaagg ccaggaaccg     480
taaaaaggcc gcgttgctgg cgttttccca taggctccgc cccccgtacg agcatcacaa     540
aaatcgacgc tcaagtcaga ggtggcgaaa cccgacagga ctataaagat accaggcgtt     600
tccccctgga agctccctcg tgcgctctcc tgttccgacc ctgccgctta ccggatacct     660
gtccgccttt ctcccttcgg gaagcgtggc gctttctcat agctcacgct gtaggtatct     720
cagttcggtg taggtcgttc gctccaagct gggctgtgtg cacgaacccc ccgttcagcc     780
cgaccgctgc gccttatccg gtaactatcg tcttgagtcc aacccggtaa gacacgactt     840
atcgccactg gcagcagcca ctggtaacag gattagcaga gcgaggtatg taggcggtgc     900
tacagagttc ttgaagtggt ggcctaacta cggctacact agaagaacag tatttggtat     960
ctgcgctctg ctgaagccag ttaccttcgg aaaaagagtt ggtagctctt gatccggcaa    1020
acaaaccacc gctggtagcg gtggtttttt tgtttgcaag cagcagatta cgcgcagaaa    1080
aaaaggatct caagaagatc ctttgatctt ttctacgggg tctgacgctc agtggaacga    1140
aaactcacgt taagggattt tggtcatgag attatcaaaa aggatcttca cctagatcct    1200
tttaaattaa aaatgaagtt ttaaatcaat ctaaagtata tatgagtaaa cttggtctga    1260
cagttaccaa tgcttaatca gtgaggcacc tatctcagcg atctgtctat ttcgttcatc    1320
catagttgcc tgactcctgc aaaccacgtt gtggtagaat tggtaaagag agtcgtgtaa    1380
aatatcgagt tcgcacatct tgttgtctga ttattgattt ttggcgaaac catttgatca    1440
tatgacaaga tgtgtatcta ccttaactta atgattttga taaaaatcat taggtaccc    1500
tgatcactgt ggaatgtgtg tcagttaggg tgtggaaagt ccccaggctc ccagcaggc    1560
agaagtatgc aaagcatgca tctcaattag tcagcaacca ggtgtggaaa gtccccaggc    1620
tccccagcag gcagaagtat gcaaagcatg catctcaatt agtcagcaac catagtcccg    1680
cccctaactc cgcccatccc gcccctaact ccgcccagga tccgctctag atggccattg    1740
catacgttgt atccatatca taatatgtac atttatattg gctcatgtcc aacattaccg    1800
ccatgttgac attgattatt gactagttat taatagtaat caattacggg gtcattagtt    1860
catagcccat atatggagtt ccgcgttaca taacttacgg taaatggccc gcctggctga    1920
ccgcccaacg acccccgccc attgacgtca ataatgacgt atgttcccat agtaacgcca    1980
atagggactt tccattgacg tcaatgggtg gagtatttac ggtaaactgc ccacttggca    2040
gtacatcaag tgtatcatat gccaagtacg cccctattg acgtcaatga cggtaaatgg    2100
cccgcctggc attatgccca gtacatgacc ttatgggact ttcctacttg gcagtacatc    2160
tacgtattag tcatcgctat taccatggtg atgcggtttt ggcagtacat caatgggcgt    2220
ggatagcggt ttgactcacg gggatttcca agtctccacc ccattgacgt caatgggagt    2280
ttgttttggc accaaaatca acgggacttt ccaaaatgtc gtaacaactc cgccccattg    2340
```

-continued

```
acgcaaatgg gcggtaggcg tgtacggtgg gaggtctata taagcagagc tcgtttagtg    2400
aaccgtcaga tcgcctggag acgccatcca cgctgttttg acctccatag aagacaccgg    2460
gaccgatcca gcctccgcgg ctcgcatctc tccttcacgc gcccgccgcc ctacctgagg    2520
ccgccatcca cgccggttga gtcgcgttct gccgcctccc gcctgtggtg cctcctgaac    2580
tgcgtccgcc gtctaggtaa gtttaaagct caggtcgaga ccgggccttt gtccggcgct    2640
cccttggagc ctacctagac tcagccggct ctccacgctt tgcctgaccc tgcttgctca    2700
actctagttc tctcgttaac ttaatgagac agatagaaac tggtcttgta gaaacagagt    2760
agtcgcctgc ttttctgcca ggtgctgact tctctcccct gggcttttt cttttctca     2820 ggttgaaaag aagaagacga agaagacgaa gaagacaaac cgtcgtcgac aagcttggta    2880
ccgagctcgg atccgccgcc accatgcaaa tctttgtgaa gacgctgacg ggaaagacca    2940
tcacgctcga agtggaaccc tcggacacga tcgaaaacgt gaaagctaag atccaggaca    3000
aggaaggaat ccccccgac cagcagagac tgatctttgc tggaaagcag ctcgaagacg     3060
gacgcacgct gtcggactac aacatccaga agaatcgac gctccacctg gtcctgagac     3120
tccgcggagc tatgcaccaa aagcgaaccg ctatgtttca ggaccccag gaacgacccc     3180 gtaaactgcc ccagctctgc acggaactgc aaacgacgat ccatgacatc atcctcgaat    3240
gcgtgtactg caagcaacag ctcctgcgac gtgaagtcta cgactttgct tttcgcgacc    3300
tgtgcatcgt ctacagagac ggaaaccct acgctgtggg agacaaatgc ctgaagtttt     3360
actcgaaaat ctcggaatac cgccactact gctactcgct gtacggaacc acgctcgaac    3420
agcaatacaa caaccccta tgcgacctgc taatccgctg catcaactgc caaaagcctc     3480
tctgccctga agaaaagcaa cgccatctcg acaaaaagca aagatttcac aacacgcgtg    3540
gacgatggac cggacgatgc atgtcgtgct gcagatcgtc acgcacgcgt agagaaaccc    3600
agctggctgg agctatgcat ggagatacgc ctacgctcca tgaatatatg ctcgatctgc    3660
aacccgaaac gaccgatctc tacggatatg gacaacttaa cgactcgtcg gaagaagaag    3720
atgaaatcga tggacccgct ggacaagctg aacccgaccg tgctcattac aacatcgtca    3780
cgttttgttg caagtgtgac tcgacgctgc gactgtgcgt ccaatcgacc cacgtggaca    3840
tccgtacgct cgaagacctg ctcatgggaa cgcttggaat cgtctgcccc atctgctcgc    3900
agaaacccta atgactcgag agatcttttt ccctctgcca aaaattatgg ggacatcatg    3960
aagccccttg agcatctgac ttctggctaa taaaggaaat ttattttcat tgcaatagtg    4020
tgttggaatt ttttgtgtct ctcactcgga aggacataag ggcggcc                  4067
```